United States Patent [19]

Eichler et al.

[11] 4,374,984
[45] Feb. 22, 1983

[54] AROMATIC-ALIPHATIC KETONES USEFUL AS PHOTOINITIATORS

[75] Inventors: Jürgen Eichler, Weiterstadt; Claus Herz, Heidelberg; Karl-Heinz Neisius; Gregor Wehner, both of Darmstadt, all of Fed. Rep. of Germany

[73] Assignee: Merck Patent Gesellschaft mit Beschrankter Haftung, Darmstadt, Fed. Rep. of Germany

[21] Appl. No.: 240,439

[22] Filed: Mar. 4, 1981

[30] Foreign Application Priority Data

Mar. 5, 1980 [DE] Fed. Rep. of Germany ....... 3008411

[51] Int. Cl.³ ................. C07D 219/06; C07D 413/06; C07D 413/14
[52] U.S. Cl. .......................... 544/80; 260/239 D; 544/121; 544/126; 544/145; 544/150; 544/154; 544/155; 544/156; 544/175; 544/357; 544/361; 546/103; 546/196; 546/200; 546/202; 546/204; 546/237; 564/328; 564/342; 568/326; 568/332; 568/333; 556/418; 556/427; 556/428; 556/436

[58] Field of Search ................... 546/103; 260/239 D; 544/80, 121, 126, 357, 361

[56] References Cited

U.S. PATENT DOCUMENTS 3,947,449 3/1976 Dürckheimer et al. ............ 546/103

Primary Examiner—Richard A. Schwartz
Attorney, Agent, or Firm—Millen & White

[57] ABSTRACT

Compounds of the formula

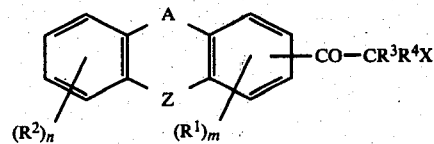

wherein the substituents A, Z, $R^1$, $R^2$, $R^3$, $R^4$, X, n and m are defined hereinbelow are effective photoinitiators, especially for the photopolymerization of ethylenically unsaturated compounds and for the curing of printing inks.

3 Claims, No Drawings

AROMATIC-ALIPHATIC KETONES USEFUL AS PHOTOINITIATORS

BACKGROUND OF THE INVENTION

The present invention relates to new aromatic-aliphatic ketones and their use as photoinitiators, in particular for the photopolymerization of ethylenically unsaturated compounds, and as UV-curing agents for printing inks, and to photopolymerizable systems containing such ketones.

Photochemically initiated polymerization reactions have achieved great importance in industry, especially where thin layers are to be cured rapidly. Examples include the curing of coatings of lacquer and resin on paper, metal and plastic and the drying of printing inks. Such photochemical processes are distinguished by a savings in raw material and energy and less pollution of the environment compared with conventional methods for printing and coating articles. Since, generally, none of the reactants in these reactions is capable of absorbing the photochemically active radiation to a sufficient extent, it is necessary to add so-called photoinitiators which are capable of absorbing incident visible or UV radiation and forming active starter radicals when being excited. According to the kind of reaction following photoexcitation two groups are differentiated: One group of initiators after being excited directly decays into active starter radicals which in turn initiate the polymerization. Another group of initiators after being excited first interreacts with a further compound to form the active starter radicals which in turn initiate the polymerization.

Essential criteria for the choice of such initiators are, inter alia, the type of reaction to be carried out, the relationship between the absorption spectrum of the initiator and the spectral energy distribution of the available source of radiation, the solubility of the initiator in the reaction mixture, the stability when stored in the dark of the reaction system to which the initiator has been added, and the effect and acceptability of the residues of the initiator remaining in the end product and/or the products formed therefrom during the photochemical reaction. In particular, the rate of reaction largely depends on the initiator used. Consequently, there has been no lack of attempts to provide new initiators which exhibit an increased reactivity with regard to their ability to initiate either the photopolymerization of ethylenically unsaturated compounds or the curing of photopolymerizable systems.

Benzophenone derivatives, benzoin ethers, benzil ketals, dibenzosuberone derivatives, anthraquinones, xanthones, thioxanthones and α-halogenoacetophenone derivatives have hitherto chiefly been employed as initiators for the photopolymerization of unsaturated compounds. However, the usefulness of these substances in industry is significantly restricted by a number of disadvantages. These include, inter alia, the low stability when stored in the dark of many photopolymerizable systems to which these initiators have been added, low chemical stability and too low a reactivity with regard to their ability to initiate the photopolymerization of ethylenically unsaturated compounds or the curing of photopolymerizable systems. In addition, many of these known initiators cause yellowing of the polymers prepared using them. This is highly undesirable, especially in the coating of light-colored substrate materials and in the case of printing inks cured by UV radiation. For the latter field of use, the frequently low solubility of the known initiators in the photopolymerizable systems is also a great disadvantage. Since printing inks as a rule contain considerable amounts of colored pigments which absorb a large proportion of the energy irradiated without producing any photochemical activity, a relatively large amount of initiator must be added to these inks. Frequently, the known initiators then partially crystallize out. Apart from the fact that the portions which have crystallized out can no longer have an initiating action, after some time the crystallites formed also damage the printing plates, which consist of relatively soft materials.

Furthermore, dialkoxyacetophenones have been described as photoinitiators in German Offenlegungsschriften Nos. 2,261,383 and 2,730,462, and a number of hydroxyalkylphenones have been described as photoinitiators in German Offenlegungsschrift No. 2,722,264. The disadvantages of the initiators known hitherto are exhibited by these compounds to a considerably lesser extent. Also, these compounds, some of which are liquid, are significantly more soluble in the customary photopolymerizable systems than are most of the initiators known hitherto, which as a rule are solid. Moreover, they have a good stability when stored in the dark and a good chemical stability. In particular, however, when these initiators are used in photopolymerization, yellowing of the polymers is observed to a considerably lesser extent than with the hitherto conventional initiators. Nevertheless, in spite of the increased photoinitiating activity of these dialkoxyacetophenones and hydroxyalkylphenones in comparison with the other known initiators, these compounds still exhibit insufficient reactivity in the initiation of photopolymerizations. Relatively long curing times are still necessary. This prevents optimum utilization of UV-radiation equipment.

SUMMARY OF THE INVENTION

Accordingly, it is an object of this invention to provide initiators, in particular for the photopolymerization of ethylenically unsaturated compounds or for the curing of photopolymerizable systems, which are physiologically acceptable; have a sufficient stability when stored in the dark as mixtures with other reactants; do not, themselves or as a result of their secondary products, cause yellowing of the reaction product; have as high a solubility as possible in the customary photopolymerizable systems; cause considerably less surface tackiness of the coatings obtained using them; and, thereby, exhibit as high a reactivity as possible with regard to their ability to initiate the curing of photopolymerizable systems, thereby being active even when used in low concentrations.

Upon further study of the specification and appended claims, further objects and advantages of this invention will become apparent to those skilled in the art.

These objects have been attained by this invention by providing, in one aspect, aromatic-aliphatic ketones of formula I

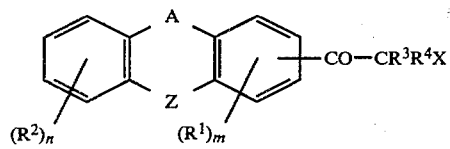

(I)

wherein

A is —CO— or —CO—CO—;

X is —OR$^5$, —OSiR$^6$(R$^7$)$_2$ or —NR$^8$R$^9$, or together with R$^3$ is —O—CH(R$^{10}$)—, —O—CH(R$^{10}$)—O—(CH$_2$)$_{1-2}$— or —O—alkylene of 1-4 C atoms, or, if R$^3$=R$^4$=OR$^{11}$, also is H;

Z is (H,H), a direct bond, —CH$_2$—, —CH$_2$—CH$_2$—, —S—, —O—, —CO— or —NR$^{12}$—;

m is 0 or an integer from 1 to 3;

n is 0 or an integer from 1 to 3;

R$^1$ is alkyl of 1-12 C atoms, cycloalkyl of 5-6 C atoms, aryl of 6-14 C atoms, aralkyl of 7-9 C atoms, —OH, —OAlk, —OAr, —SAlk, —SCH$_2$CH$_2$OH, —SAr, —SO$_2$Alk, —SO$_2$phenyl, —SO$_2$NH$_2$, —SO$_2$NHAlk, —SO$_2$N(Alk)$_2$, —COOAlk, —NH$_2$, —NHAlk, —N(Alk)$_2$, —NHCOphenyl, —CN or halogen;

R$^2$ can be any of the groups given for R$^1$ or is another —CO—CR$^3$R$^4$X group;

R$^3$ is H, alkyl of 1-8 C atoms, alkyl of 1-8 C atoms substituted by —OH, —OAlk, acyloxy of 2-8 C atoms, —NR$^8$R$^9$, —COOAlk or —CN, or is alkenyl of 3-5 C atoms, cycloalkyl of 5-6 C atoms or aralkyl of 7-9 C atoms; or, if X=H and R$^3$=R$^4$, also is —OR$^{11}$;

R$^4$ can be any of the groups given for R$^3$ or —CH$_2$CH$_2$R$^{13}$, or, together with R$^3$ is alkylene of 2-8 C atoms or oxa- or aza-alkylene of 3-9 C atoms, or, together with R$^9$, is alkylene of 1-9 C atoms, phenylalkylene or oxa- or aza-alkylene of 2-3 C atoms, or, if X=H and R$^3$=R$^4$, also is —OR$^{11}$;

R$^5$ is H, alkyl of 1-12 C atoms, alkyl of 1-8 C atoms substituted by —Cl, —Br, —OH, —OAlk, —SAlk, acyloxy of 2-8 C atoms, —COOAlk, —CONHAlk, —CON(Alk)$_2$ or —CN, or is alkenyl of 3-5 C atoms, cyclohexyl, benzyl, phenyl, phenyl substituted by —Cl or —Alk, or 2-tetrahydropyranyl;

R$^6$ and R$^7$, which can be identical or different, are alkyl of 1-4 C atoms or phenyl;

R$^8$ is alkyl of 1-12 C atoms, alkyl of 2-4 C atoms substituted by —OH, —OAlk or —CN, or is alkenyl of 3-5 C atoms, cyclohexyl, aralkyl of 7-9 C atoms, phenyl or phenyl substituted by —Cl, —Alk, —OH, —OAlk or —COOAlk;

R$^9$ is alkyl of 1-12 C atoms, alkyl of 2-4 C atoms substituted by —OH, —OAlk or —CN, or is alkenyl of 3-5 C atoms, cyclohexyl or aralkyl of 7-9 C atoms, or, together with R$^8$, is alkylene of 4-5 C atoms optionally interrupted by —O— or —NR$^{14}$—, or, together with R$^4$, is alkylene of 1-9 C atoms, phenylalkylene or oxa- or aza-alkylene of 2-3 C atoms;

R$^{10}$ is H, alkyl of 1-8 C atoms or aryl of 6-14 C atoms;

R$^{11}$ is alkyl of 1-4 C atoms, alkoxyalkyl of 3-6 C atoms, C$_{1-4}$-alkyl—OCH$_2$CH$_2$OCH$_2$CH$_2$— or chloroalkyl of 2-3 C atoms;

R$^{12}$ is H, alkyl or 1-4 C atoms or cycloalkyl of 5-6 C atoms;

R$^{13}$ is —CONH$_2$, —CONHAlk, —CON(Alk)$_2$, —P-(O)(OAlk)$_2$ 2-pyridyl or 2-oxo-1-pyrrolidinyl;

R$^{14}$ is alkyl of 1-4 C atoms, —CH$_2$CH$_2$CN or —CH$_2$CH$_2$COOAlk;

Alk is alkyl of 1-4 C atoms; and

Ar is C$_{6-14}$ aryl or aryl substituted by alkyl and having a total of 6-14 C atoms. Throughout the foregoing, Ar is hydrocarbon aryl.

In another aspect, this invention also relates to the use of the aromatic-aliphatic ketones of this invention as photoinitiators, in particular for the photopolymerization of ethylenically unsaturated compounds, and as UV-curing agents for printing inks.

The present invention furthermore relates in another aspect to photopolymerizable systems containing at least one ethylenically unsaturated photopolymerizable compound and, if appropriate, other known and customary additives, which contain as photoinitiator at least one compound of this invention, preferably 0.1 to 20% by weight thereof based on the weight of the system to be polymerized.

The invention also relates in yet another aspect to a process for photopolymerizing ethylenically unsaturated compounds, comprising, before the photopolymerization is triggered off, adding at least one compound of this invention as a photoinitiator, preferably 0.1 to 20% thereof, to the system to be polymerized.

DETAILED DISCUSSION

The aromatic-aliphatic ketones of this invention, compared with the photoinitiators known hitherto, exhibit an increased reactivity with regard to their ability to initiate the curing of photopolymerizable systems. Moreover, the compounds of this invention have a good stability when stored in the dark as mixtures with the other reactants. They have a broader absorption spectrum, enabling better utilization of the electromagnetic energy irradiated by the radiation source and the use of doped lamps as radiation sources based on bathochromic shifts of the absorption maximum of the compounds of this invention.

The coatings obtained using these initiators have a considerably lower surface-tackiness than coatings obtained with conventional photoinitiators. In addition, polymers cured using the compounds of this invention are distinguished by a complete absence of yellowing or by only a very slight tendency to yellowing.

These aromatic-aliphatic ketones which are substituted on their aliphatic portions by hydroxy groups or amino groups or etherification or silylation products thereof, and which have on their aromatic portions at least one additional carbonyl group and optionally fused-on rings, which can also contain a hetero-atom, are distinguished by a surprisingly increased reactivity as photoinitiators, in particular by an increased surface hardness and the absence of yellowing, or a very slight tendency to yellowing, of the cured polymers. Moreover, the coatings obtained using these photoinitiators have a considerably lower surface-tackiness than coatings obtained with conventional photoinitiators.

In formula I, A is preferably —CO—, but also —CO—CO—.

X is preferably —OR$^5$, —OSiR$^6$(R$^7$)$_2$ or —NR$^8$R$^9$, but also, together with R$^3$, —O—CH(R$^{10}$)—, —O—CH(R$^{10}$)—O—(Ch$_2$)$_{1-2}$—or —O—alkylene of 1-4 C atoms.

Compounds in which X=H and R$^3$=R$^4$=OR$^{11}$ are also particularly advantageous.

Z is (H,H), a direct bond, —CH$_2$—, —CH$_2$—CH$_2$—, —S—, —O—, —CO— or —NR$^{12}$—, in which R$^{12}$ is H, alkyl of 1-4 C atoms, such as methyl, ethyl, propyl, i-propyl, butyl or tert-butyl, or cycloalkyl of 5-6 C atoms, such as cyclopentyl, 2-methylcyclopentyl or cyclohexyl. $R^{12}$ is preferably H, methyl or ethyl.

Compounds in which Z is (H,H) are very particularly advantageous.

m is preferably 0, and also preferably 1, but also 2 or 3.

n is preferably 0 or 1, but also 2 or 3.

The radicals $R^1$ and $R^2$, which can be identical or different, are preferably branched or straight-chain alkyl of 1–12 C atoms, phenyl, —OH, —OAlk, —SAlk, —N(Alk)$_2$ or halogen, but also cycloalkyl of 5–6 C atoms, aryl of 6–14 C atoms, aralkyl of 7–9 C atoms, —OAr, —SCH$_2$CH$_2$OH, —SAr, —SO$_2$Alk, —SO$_2$phenyl, —SO$_2$NH$_2$, —SO$_2$NHAlk, —SO$_2$N(Alk)$_2$, —COOAlk, —NH$_2$, —NHAlk, —NHCOphenyl or —CN. Alk is a branched or straight-chain lower alkyl radical of 1–4 C atoms, such as methyl, ethyl, propyl, i-propyl, butyl or tert-butyl. Ar is an aryl radical which is unsubstituted or substituted by alkyl groups and has 6–14 C atoms, such as phenyl, tolyl, xylyl, naphthyl or 2-ethylnaphthyl, preferably phenyl.

Accordingly, $R^1$ and $R^2$ can be, for example, methyl, ethyl, propyl, i-propyl, butyl, tert-butyl, pentyl, hexyl, heptyl, octyl, 2-ethylhexyl, nonyl, decyl or dodecyl; cyclopentyl, 2-methylcyclopentyl or cyclohexyl; phenyl, tolyl, xylyl, ethylphenyl or naphthyl; benzyl, phenylethyl, phenylpropyl or dimethylbenzyl; hydroxyl; methoxy, ethoxy, propoxy, butoxy or tert-butoxy; phenoxy or naphthyloxy; methylthio, ethylthio, propylthio, butylthio or tert-butylthio; 2-hydroxyethylthio; phenylthio or naphthylthio; methylsulfonyl or ethylsulfonyl; phenylsulfonyl; aminosulfonyl, methylaminosulfonyl, ethylaminosulfonyl, dimethylaminosulfonyl or diethylaminosulfonyl; methoxycarbonyl or ethoxycarbonyl; amino; methylamino, ethylamino or butylamino; dimethylamino or diethylamino; benzoylamino; cyano; or chlorine or bromine.

Compounds in which $R^2$ is another —CO—CR$^3$R$^4$X group, which is preferably identical to the —CO—CR$^3$R$^4$X group already present in the molecule, are also particularly preferred.

In the case of polysubstitution of the aromatic rings, the substituents $R^1$ and $R^2$ are preferably identical, but they can also be different.

In the case of benzophenone derivatives [A=—CO—, Z=(H,H)] and in the case of benzil derivatives [A=—CO—CO—, Z=(H,H)], the substituent(s) $R^1$ is (are) preferably in the 2-position, but also in the 3-position or 4-position, and the substituent(s) $R^2$ is (are) preferably in the 4'-position, but also in the 3'-position or 2'-position. In all the other compounds, $R^1$ is preferably in the 1-position or 4-position, but also in the 2-position or 3-position. In compounds in which A=—CO— and Z= a direct bond, —CH$_2$—, —CH$_2$CH$_2$—, —S—, —O—, —CO— or —NR$^{12}$—, and in the case of compounds in which A=—CO—CO— and Z= a direct bond, $R^2$ is preferably in the 7-position, but also in the 6-position, 5-position or 8-position; in the case of compounds in which A=—CO—CO— and Z=—CH$_2$—, —S—, —O—, —CO— or —NR$^{12}$—, $R^2$ is preferably in the 8-position, but also in the 7-position, 6-position or 9-position, while in the case of compounds in which A=—CO—CO— and Z=—CH$_2$—CH$_2$—, $R^2$ is preferably in the 9-position, and also in the 8-position, 7-position or 10-position.

$R^3$ and $R^4$, which can be identical or different, are preferably unsubstituted alkyl groups of 1–6 C atoms, but also hydrogen, alkyl groups of 7–8 C atoms, alkyl of 1–8 C atoms substituted by —OH, —OAlk, acyloxy of 2–8 C atoms (it being possible for the acyl radical to be derived from an aliphatic or aromatic carboxylic acid, e.g., a hydrocarbon such acid), —NR$^8$R$^9$, —COOAlk or —CN, or alkenyl of 3–5 C atoms, cycloalkyl of 5–6 C atoms or aralkyl of 7–9 C atoms. $R^4$ can additionally be ethyl which is further substituted by —CONH$_2$, —CONHAlk, —CON(Alk)$_2$, —P(O)(OAlk)$_2$, 2-pyridyl or 2-oxo-1-pyrrolidinyl (Alk representing a branched or straight-chain lower alkyl radical of 1–4 C atoms). Compounds in which $R^3$ and $R^4$ together are alkylene of 2–8 C atoms or oxa- or aza-alkylene of 3–9 C atoms, in particular alkylene of 4–5 C atoms or oxa- or aza-alkylene of 3–4 C atoms, are also preferred.

The invention also relates, in particular, to compounds in which, if X=H, $R^3$=$R^4$=OR$^{11}$. In these compounds, $R^{11}$ is, in particular, alkyl of 1–4 C atoms, but also alkoxyalkyl of 3–6 C atoms, alkyl—OCH$_2$CH$_2$OCH$_2$CH$_2$—, the alkyl radical having 1–4 C atoms, or chloroalkyl of 2–3 C atoms.

Accordingly, $R^3$ and $R^4$ can be, for example, the following: methyl, ethyl, propyl, i-propyl, butyl, tert-butyl, pentyl, hexyl, heptyl, octyl or 2-ethylhexyl; hydrogen; hydroxymethyl; 1-hydroxyethyl, 2-hydroxyethyl, 1-hydroxybutyl or 1-hydroxyoctyl; methoxymethyl, 1-methoxyethyl, 1-isopropoxyethyl, 1-isobutoxyethyl or 1-ethoxypropyl; 1-acetoxyethyl, 1-n-butanoyloxyethyl, 1-acryloyloxybutyl or 1-benzoyloxyhexyl; diethylaminomethyl, 1-dibutylaminoethyl or 1-dimethylaminobutyl; 2-pyrrolidinoethyl or 2-piperidinoethyl; ethoxycarbonylmethyl, 2-butoxycarbonylethyl, 3-methoxycarbonylpropyl or 2-ethoxycarbonyl-2,2-dimethylethyl; cyanomethyl, 2-cyanoethyl or 4-cyanobutyl; allyl, 2-butenyl, methallyl or 2-pentenyl; cyclopentyl, 2-methylcyclopentyl or cyclohexyl; or benzyl, 2-phenylethyl, 3-phenylpropyl or dimethylbenzyl.

$R^3$ and $R^4$, together with the carbon atom to which they are bonded, can also form, for example, a cyclopentane, cyclohexane, cycloheptane, tetrahydrofuran, tetrahydropyran, pyrrolidine or piperidine ring.

If X=H, $R^3$ and $R^4$ (which in this case are identical) can also be, for example, methoxy, ethoxy, propoxy, i-propoxy, butoxy or tert-butoxy; 2-methoxyethoxy, ethoxymethoxy, 2-ethoxyethoxy, 2-ethoxypropoxy or 2-ethoxybutoxy; CH$_3$OCH$_2$CH$_2$OCH$_2$CH$_2$O— or C$_4$H$_9$OCH$_2$CH$_2$OCH$_2$CH$_2$O—; or chloroethyl or chloropropyl.

$R^5$ is preferably hydrogen, branched or straight-chain alkyl of 1–4 C atoms, alkenyl or 3–5 C atoms, cyclohexyl, phenyl or benzyl, but also branched or straight-chain alkyl of 5–12 C atoms, alkyl of 1–8 C atoms and substituted by Cl, Br, —OH, —OAlk, —SAlk, acyloxy of 2–8 C atoms (it being possible for the acyl radical to be the radical of an aliphatic or aromatic carboxylic acid, e.g., a hydrocarbon such acid), —COOAlk, —CONHAlk, —CON(Alk)$_2$ or —CN, or phenyl which is substituted by Cl or Alk, or 2-tetrahydropyranyl, Alk being as already defined above.

Accordingly, examples of X=OR$^5$ include hydroxyl, methoxy, ethoxy, propoxy, i-propoxy, butoxy, tert-butoxy, pentyloxy, hexyloxy, octyloxy, 2-ethylhexyloxy, n-decyloxy or n-dodecyloxy; allyloxy, 2-butenyloxy or methallyloxy; cyclohexyloxy; phenoxy; benzyloxy; 2-chloroethoxy or 4-chlorobutoxy; bromomethoxy or 5-bromohexyloxy, hydroxymethoxy, 2-hydroxyethoxy, 4-hydroxybutoxy or 8-hydroxyoctyloxy; methoxymethoxy, 2-ethoxyethoxy, 2-isobutoxyethoxy or 3-methoxypropoxy; ethylthiomethoxy, 3-methylthiopropoxy or 2-tert-butyl-thioethoxy; 2-acetoxyethoxy, 2-n-butanoyloxyethoxy or 4-acryloyloxybutoxy; 6-benzoyloxyhexyloxy; ethoxycarbonylmethoxy, 2-butoxycarbonylethoxy or 3-methoxycarbonylpropoxy; 2-methylaminocarbonylmethoxy, butylaminocarbonylmethoxy or 2-dimethylaminocarbonylethoxy; 2-cyanoethoxy or 4-cyanobutoxy; 4-chlorophenoxy, 2-chlorophenoxy, 4-tolyloxy, 3-tolyloxy or 4-tert-butyl-phenoxy; or tetrahydropyranyloxy.

$R^6$ and $R^7$, which can be identical or different, are alkyl of 1–4 C atoms, such as methyl, ethyl, propyl, i-propyl, butyl and tert-butyl, or phenyl.

Accordingly, preferred meanings of $X=-OSiR^6(R^7)_2$ are trimethylsilyloxy, triethylsilyloxy, tert-butyldimethylsilyloxy and phenyl-dimethylsilyloxy.

$R^8$ and $R^9$, which can be identical or different, are preferably alkyl of 1–4 C atoms or alkyl of 2–4 C atoms substituted by —OH, —OAlk or —CN, but also alkyl of 5–12 C atoms, alkenyl of 3–5 C atoms, cyclohexyl or aralkyl of 7–9 C atoms. $R^8$ can furthermore be phenyl or phenyl substituted by —Cl, —Alk, —OH, —OAlk or —COOAlk, Alk being as defined above. Compounds in which $R^8$ and $R^9$ together form an alkylene radical which has 4–5 C atoms and can be interrupted by —O— or —$NR^{14}$— are also particularly advantageous. $R^{14}$ is alkyl of 1–4 C atoms, in particular alkyl of 1–2 C atoms, but also 2-cyanoethyl or —CH$_2$CH$_2$—COOAlk, such as 2-methoxycarbonylethyl, 2-ethoxycarbonylethyl or 2-tert-butoxycarbonylethyl. Furthermore, $R^9$, together with $R^4$, can be alkylene of 1–9 C atoms, phenylalkylene or oxa- or aza-alkylene of 2–3 C atoms.

$R^8$ and $R^9$ can thus be, for example, methyl, ethyl, propyl, i-propyl, butyl, tert-butyl, pentyl, hexyl, octyl, 2-ethylhexyl, n-decyl or n-dodecyl; 2-hydroxyethyl or 2-hydroxybutyl; 2-methoxyethyl, 2-ethoxypropyl or 2-butoxyethyl; 2-cyanoethyl; allyl, 2-butenyl, methallyl or 2-pentenyl; cyclohexyl; or benzyl, 2-phenylethyl, 3-phenylpropyl or dimethylbenzyl. $R^8$ can furthermore be, for example, phenyl, 4-chlorophenyl, 2-tolyl, 4-ethylphenyl, 3-hydroxyphenyl, 2-methoxyphenyl, 4-butoxyphenyl, 4-ethoxycarbonylphenyl or 4-chloro-2-tolyl. If $R^8$ and $R^9$, together with the N atom to which they are bonded, form a ring, it is, for example, a pyrrolidine, piperidine, morpholine, piperazine, 4-alkylpiperazine, 4-cyanoethylpiperazine or 4-alkoxycarbonylethylpiperazine ring. If $R^9$ and $R^4$, together with the C atom to which $R^4$ is bonded, form a ring, it is, for example, a pyrrolidine, 3-phenyl-pyrrolidine, imidazolidine, piperidine, 3-phenylpiperidine, piperazine or morpholine ring.

Preferred meanings of $X=-NR^8R^9$ are, for example, dimethylamino, diethylamino, dibutylamino, methylhexylamino or ethyloctylamino; or di-(2-hydroxyethyl)-amino, di-(2-methoxyethyl)-amino, di-(2-cyanoethyl)-amino, diallylamino, cyclohexylmethylamino, benzylmethylamino, methylphenylamino, methyltolylamino, 4-ethoxycarbonylphenylmethylamino, pyrrolidino, piperidino, 2-methylpiperidino, morpholino, piperazino, 4-methylpiperazino or 4-ethoxycarbonylethylpiperazino.

$R^{10}$ is preferably hydrogen or alkyl of 1–4 C atoms, but also alkyl of 5–8 C atoms or aryl which is substituted or unsubstituted by alkyl groups and has a total of 6–14 C atoms. Examples of $R^{10}$ are, in addition to hydrogen, methyl, ethyl, propyl, butyl, tert-butyl, hexyl, octyl, phenyl, tolyl, 4-ethylphenyl, naphthyl or 2-methylnaphthyl.

X and $R^3$, together with the C atom to which they are bonded, can consequently form an oxirane, methyl-oxirane, phenyloxirane, 1,3-dioxane, 2-methyl-1,3-dioxane, 2-phenyl-1,3-dioxane, 1,3-dioxolane, 2-methyl-1,3-dioxolane, tetrahydrofuran or tetrahydropyran ring.

If the compounds of formula I of this invention are benzophenone derivatives [A=—CO—, Z=(H,H)] or benzil derivatives [A=—CO—CO—, Z=(H,H)], the substituent —CO—CR$^3$R$^4$X is preferably in the 4-position, but it can also be in the 3-position or 2-position. In all the other compounds of the formula I (A=—CO— or —CO—CO—, Z= a direct bond, —CH$_2$—, —CH$_2$—CH$_2$—, —S—, —O—, —CO— or —NR$^{12}$—), the substituent —CO—CR$^3$R$^4$X is preferably in the 2-position, but it can also be in the 3-position, 4-position or 1-position.

Accordingly, compounds of formula I which are particularly preferred according to this invention are those in which at least one of the symbols A, X, Z, m, n, $R^1$ to $R^{14}$, Alk and Ar has one of the above-mentioned preferred meanings. In preferred compounds of formula I, A is —CO— or —CO—CO—; X is —OR$^5$, —OSiR$^6$(R$^7$)$_2$ or —NR$^8$R$^9$, or, together with $R^3$, —O—CH(R$^{10}$)—O—(CH$_2$)$_{1-2}$— or —O-alkylene of 1–4 C atoms, or, if $R^3$=$R^4$=OR$^{11}$, also H; Z is (H,H), a direct bond, —CH$_2$—, —CH$_2$CH$_2$—, —S—, —O—, —CO— or —NR$^{12}$—; m is 0 or 1; n is 0 or 1; $R^1$ is alkyl of 1–8 C atoms, cycloalkyl of 5–6 C atoms, aryl of 6–10 C atoms, aralkyl of 7–9 C atoms, —OAlk, —OAr, —SAlk, —COOAlk, —NH$_2$, —NHAlk, —N(Alk)$_2$, —CN or halogen; $R^2$ is one of the groups defined for $R^1$ or is another —CO—CR$^3$R$^4$X group; $R^3$ is H, alkyl of 1–8 C atoms, alkyl of 1–4 C atoms substituted by —OH, —OAlk, —NR$^8$R$^9$ or —CN, or alkenyl of 3–5 C atoms, or if X=H and $R^3$=$R^4$, also —OR$^{11}$; $R^4$ is one of the groups defined for $R^3$, or together with $R^3$, is alkylene of 4–6 C atoms or oxa- or aza-alkylene of 3–5 C atoms, or, if X=H and $R^3$=$R^4$, also —OR$^{11}$; $R^5$ is H, alkyl of 1–8 C atoms, alkyl of 1–8 C atoms substituted by —OH, —OAlk, —SAlk, —COOAlk or —CN, or alkenyl of 3–5 C atoms, cyclohexyl, benzyl, phenyl or tetrahydropyranyl; $R^6$ and $R^7$, which can be identical or different, are alkyl of 1–4 C atoms or phenyl; $R^8$ is alkyl of 1–8 C atoms, alkyl of 2–4 C atoms substituted by —OH, —OAlk, or —CN, or alkenyl of 3–5 C atoms, benzyl or phenyl; $R^9$ is alkyl of 1–8 C atoms, alkyl of 2–4 C atoms substituted by —OH, —OAlk or —CN, or alkenyl of 3–5 C atoms or benzyl, or, together with $R^8$, alkylene of 4–5 C atoms which can be interrupted by —O— or —NR$^{14}$—; $R^{10}$ is H or alkyl of 1–4 C atoms; $R^{11}$ is alkyl of 1–4 C atoms or alkoxyalkyl of 3–6 C atoms; $R^{12}$ is H or alkyl of 1–4 C atoms; $R^{14}$ is alkyl of 1–4 C atoms; Alk is alkyl of 1–4 C atoms; and Ar is $C_{6-10}$-aryl or aryl substituted by alkyl groups and having a total of 6–10 C atoms.

The use of these compounds as photoinitiators is likewise particularly preferred.

Very particularly preferred compounds of formula I are those in which A is —CO—; X is —OR$^5$, —OSiR$^6$(R$^7$)$_2$ or —NR$^8$R$^9$, or, if $R^3$=$R^4$=OR$^{11}$, also H; Z is (H,H), a direct bond, —CH$_2$—, —CH$_2$—CH$_2$—, —S—, —O—, —CO— or NR$^{12}$; m is 0 or 1; n is 0 or 1; $R^1$ is alkyl of 1–4 C atoms, phenyl, —OAlk, —SAlk, —N(Alk)$_2$ or halogen; $R^2$ is one of these groups defined for $R^1$ or is another —CO—CR$^3$R$^4$X group; $R^3$ is H or alkyl of 1–6 C atoms, or, if X=H and $R^3$=$R^4$, also —$OR^{11}$; $R^4$ is one of these groups defined for $R^3$, or, together with $R^3$, is alkylene of 4–6 C atoms, or, if X=H and $R^3$=$R^4$, also —$OR^{11}$; $R^5$ is H, alkyl of 1–4 C atoms, alkenyl of 3–5 C atoms, cyclohexyl, benzyl, phenyl or 2-tetrahydropyranyl; $R^6$ and $R^7$, which can be identical or different, are alkyl of 1–4 C atoms or phenyl; $R^8$ is alkyl of 1–4 C atoms, alkyl of 2–4 C atoms substituted by —OH, —OAlk or —CN, or phenyl or benzyl; $R^9$ is alkyl of 1–4 C atoms, alkyl of 2–4 C atoms substituted by —OH, —OAlk or —CN, or phenyl or benzyl, or, together with $R^8$, alkylene of 4–5 C atoms which can be interrupted by —O— or —$NR^{14}$—; $R^{11}$ is alkyl of 1–4 C atoms; $R^{12}$ is H or alkyl of 1–4 C atoms; $R^{14}$ is alkyl of 1–4 C atoms and Alk is alkyl of 1–4 C atoms.

The use of these compounds as photoinitiators is likewise very particularly preferred.

The compounds of formula I can be prepared by standard processes of organic chemistry. The reaction conditions can be found in the standard works of preparative organic chemistry, for example, HOUBEN-WEYL, Methoden der organischen Chemie (Methods of Organic Chemistry), Georg Thieme Verlag, Stuttgart, or ORGANIC SYNTHESES, J. Wiley, New York-London-Sydney.

Compounds of formula I in which X=—OH or —$NR^8R^9$ and A, Z, m, n, $R^1$ to $R^4$, $R^8$, $R^9$, $R^{12}$ to $R^{14}$, Alk and Ar are as defined above, can be prepared, for example, by converting an α-halogeno-ketone of formula II

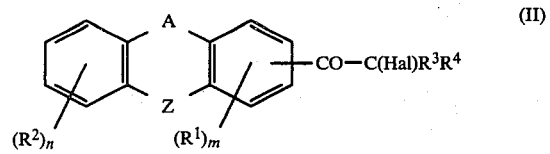

(II)

wherein Hal is a halogen atom, preferably chlorine or bromine, and A, Z, m, n and $R^1$ to $R^4$ are as defined above, into a compound of formula I in which X=—OH or —$NR^8R^9$ in a manner which is customary per se, by reaction with a compound of the formula WX, wherein W is H or, if X=—OH, also one equivalent of an alkali metal or alkaline earth metal atom, and X is —OH or —$NR^8R^9$.

The α-halogeno-ketones of formula II used as starting materials can be prepared, for example, via the following reaction stages:

A compound of formula III

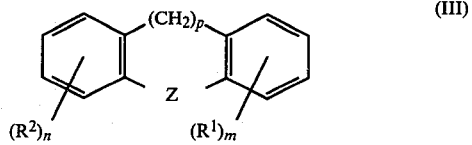

(III)

wherein p is 1 or 2 and Z, m, n, $R^1$ and $R^2$ are as defined above, is reacted with an α-halogenocarboxylic acid halide of formula IVa Hal—CO—C(Hal)$R^3R^4$ (IVa)

wherein Hal is a halogen atom, preferably chlorine or bromine, and $R^3$ and $R^4$ are as defined above, in the presence of a Lewis acid, for example, aluminum chloride, and the α-halogeno-ketone thus obtained, of formula Va

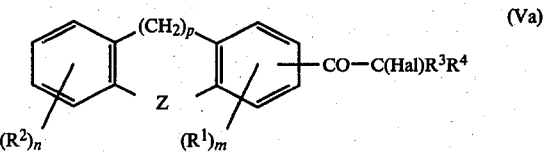

(Va)

wherein Hal, Z, m, n, p and $R^1$ to $R^4$ are as defined above, is oxidized to give a compound of formula II.

Suitable oxidizing agents are the known oxidizing agents, such as, for example, nitric acid, oxygen, per-compounds, such as hydrogen peroxide, a metal peroxide, or inorganic or organic peracids, selenium dioxide, hypochlorous acids, chloric acid, periodic acid and metal compounds of higher valency stages, such as iron-III compounds, manganese dioxide, potassium permanganate, chromic acid, chromic anhydride, chromates, lead dioxide or lead tetraacetate. The oxidation is preferably carried out in a solvent, such as, for example, acetic acid, dimethylformamide, benzene, halogenobenzenes, methylene chloride or chloroform, at temperatures from 20° to the boiling point of the solvent or of the mixture to be oxidized.

Instead of the reaction with α-halogenocarboxylic acid halides of formula IVa, it is also possible, especially if these compounds are only accessible with difficulty, to react the compounds of formula III with carboxylic acid halides of formula IVb Hal—CO—CHR$^3R^4$ (IVb)

wherein Hal, $R^3$ and $R^4$ are as defined above, and to oxidize the ketones thus obtained, of formula Vb

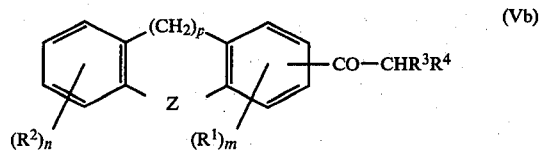

(Vb)

as described above.

The halogenation, preferably the chlorination or bromination, of the aliphatic C atom adjacent to the keto group can be carried out before or after the oxidation of the compound of formula Vb. Possible halogenating agents are, for example, chlorine, bromine or sulfuryl chloride. The halogenation is advantageously carried out in an inert solvent, preferably in CCl$_4$, at temperatures from 40° to 80°, preferably at about 60°.

This procedure is preferably followed if the carboxylic acid halide of formula IVb is readily accessible and no side reactions can occur during the halogenation, for example, halogenation of carbon atoms in benzyl radicals in $R^1$ and/or $R^2$.

The starting compounds of formula II can also be obtained by reacting a compound of formula VI

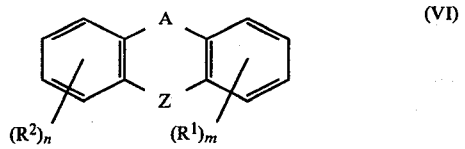

(VI)

with a compound of formula IVa or IVb in the manner described above and, if appropriate, halogenating the resulting compound.

The reaction of the α-halogeno-ketone of formula II with a compound of the formula WX is carried out in a manner which is known per se. If $R^3$ and $R^4$ are alkyl groups, this reaction is effected even by simply heating the α-halogeno-ketone (II) in an excess of a dilute or concentrated solution of an alkali metal hydroxide in water or a watermiscible solvent, such as, for example, methanol, ethanol, propanol, isopropanol, acetone or dimethylsulfoxide, or by heating the α-halogeno-ketone (II) with at least 2 molar equivalents of the corresponding amine $HNR^8R^9$ to 100° to 200°. This heating is carried out in the absence or in the presence of an inert solvent, such as, for example, toluene or xylene. It is particularly preferably to use an excess of the amine as the solvent. In the case of low-boiling amines, such as, for example, dimethylamine or diethylamine, the reaction is preferably carried out under pressure.

In many cases, however, it is more preferable first to convert the α-halogeno-ketone of formula II into the corresponding epoxide of formula VII

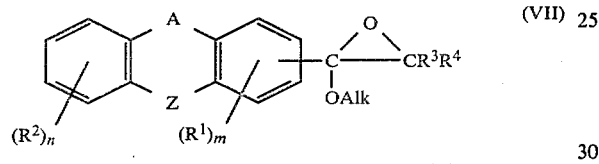

(VII)

wherein A, Z, m, n, $R^1$ to $R^4$ and Alk are as defined above, and to react this epoxide, by means of hydrolysis or aminolysis, to produce compounds of formula I in which $X$=—OH or —$NR^8R^9$.

In order to prepare the epoxide intermediate products, the α-halogeno-ketone of formula II is reacted with a stoichiometric amount of an alkali metal alkoxide, for example, sodium methoxide or sodium ethoxide, in an inert solvent, for example a lower alcohol with 1-4 C atoms.

The hydrolysis to give compounds of formula I in which $X$=—OH is preferably effected by heating the epoxides in an excess of water, with the addition of a catalytic amount of mineral acid. Aminolysis of the epoxides to produce compounds of formula I in which $X$=$NR^8R^9$ is carried out, for example, by adding a stoichiometric amount of the corresponding amine and heating the reaction mixture to 100° to 200°. No solvent is added, or the reaction is carried out in the presence of a small amount of an inert solvent, such as, for example, toluene or xylene. In the case of low-boiling amines, such as, for example, dimethylamine or diethylamine, the reaction is preferably carried out under pressure.

It may furthermore be preferable, especially if one or both of the radicals $R^3$ and $R^4$ are hydrogen, first to convert the α-halogeno-ketone (II) into the corresponding alkanoyloxy-ketone, for example, into the corresponding acetoxy-ketone, by reaction with a carboxylic acid salt, for example, sodium acetate, in an anhydrous organic solvent, and to convert this product into the corresponding compound of formula I in which $X$=—OH or —$NR^8R^9$ by hydrolysis in the presence of a weakly basic compound, for example, sodium bicarbonate, or by aminolysis.

The aromatic-aliphatic ketones of formula I in which $X$=—OH which can thus be obtained can be etherified or O-silylated by the customary methods, to give compounds of the general formula I in which $X$=—$OR^5$ or —$OSiR^6(R^7)_2$, $R^5$ to $R^7$ being as defined above. The etherifying agents preferably used are alkyl halides of formula $R^5$-Hal, wherein $R^5$ and Hal are as defined above, but the corresponding dialkyl sulfates or alkyl arylsulfonates are also suitable. Examples of etherifying agents are methyl iodide, ethyl iodide, tert-butyl bromide, allyl bromide, cyclohexyl bromide, benzyl chloride, ethyl chloroacetate, diethyl sulfate or methyl phenylsulfonate. The etherification is preferably carried out in an inert solvent, with the addition of the equivalent amount of an alkali metal hydroxide.

The compounds of formula I in which $X$=—$OR^5$ and $R^5$=unsubstituted or substituted alkyl can also be prepared, for example, by reacting the α-halogeno-ketones (II) with an alcoholate, for example, sodium ethylate, in an anhydrous organic solvent, such as, for example, ethanol.

Compounds of formula I in which $R^3$ or $R^4$ is a substituted alkyl group can furthermore be prepared from compounds of formula VIIIa or VIIIb

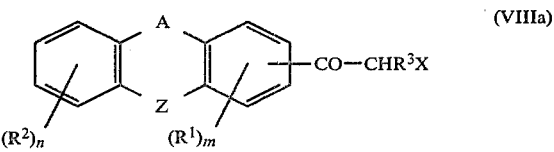

(VIIIa)

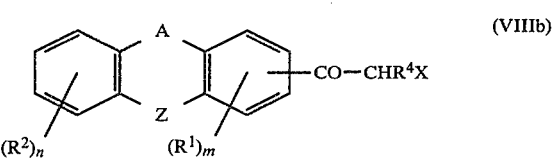

(VIIIb)

by reaction with aldehydes or with a vinyl compound capable of undergoing addition reactions, such as, for example, acrylates or acrylonitrile. The group $R^4$=—$CH_2CH_2R^{13}$ can be introduced in an analogous manner, starting from a compound of formula VIIIa. In the case where $R^3$ and $R^4$ are identical and denote substituted alkyl, both substituents can be introduced together by reacting a compound of formula VIIIc

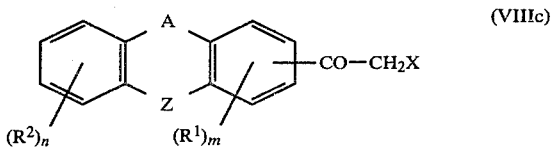

(VIIIc)

with at least 20 moles of an aldehyde or a vinyl compound capable of undergoing addition reactions.

The corresponding alkoxyalkyl and acyloxyalkyl groups can be obtained from the hydroxyalkyl groups $R^3$ and/or $R^4$ by etherification or esterification.

Compounds of formula I in which $R^3$ and/or $R^4$ are aminoalkyl groups can be prepared from compounds of formula VIIIa, VIIIb or VIIIc by reaction with 1 or 2 moles of formaldehyde and a secondary amine in a so-called Mannich reaction. Compounds of formula I in which X and $R^3$ together are an —O—$CH(R^{10})$— group can furthermore be prepared from the corresponding α-vinyl-ketones by epoxidization. The compounds which can be obtained in this manner can be converted into compounds of formula I in which $X$=—OH and $R^3$ or $R^4$ is an aminoalkyl group or X=—NR$^8$R$^9$ and R$^3$ or R$^4$ is a hydroxyalkyl group by reaction with secondary amines.

Compounds of formula I in which R$^9$ and R$^4$ together are an alkylene group of 1–9 C atoms can be obtained from α,β-dibromo-ketones of formula IX

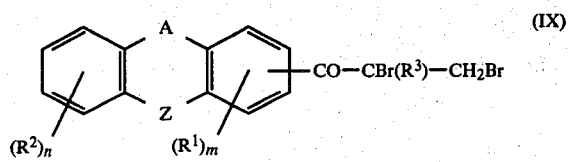

(which can be obtained by adding bromine onto the correspoinding α-vinyl-ketons) by reaction with one mole of a primary amine, while the corresponding compounds of formula I in which X=—NR$^8$R$^9$ and R$^4$ is an aminoalkyl radical are obtained by reaction of the α,β-dibromo-ketones with 2 moles of a secondary amine.

In some cases, it is also possible for the substituent X already to be introduced in a ketone synthesis by a Friedel-Crafts reaction. For this, a compound of formula VI which has already been mentioned above is reacted with a compound of formula X

Hal—CO—CR$^3$R$^4$X     (X)

in a manner which is known per se. However, this process variant can only be used in cases in which the substituent X is not attacked under the reaction conditions of the Friedel-Crafts reaction. This process is suitable, for example, for the preparation of compounds of formula I in which X and R$^3$, together with the C atom to which they are bonded, form a heterocyclic ring. Heterocyclic carboxylic acid halides are used as the compound of formula X.

The compounds of formula I in which X=H, R$^3$=R$^4$=OR$^{11}$ and R$^{11}$ is as defined above, can likewise be prepared by processes which are known per se. In a preferred preparation process, the acetyl compounds of formula XI

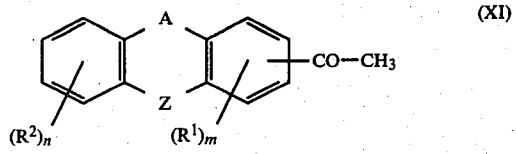

are oxidized with, for example, selenium dioxide to give the correspoding α-ketoaldehydes (compare, for example, Org. Syntheses, Volume II, (1943), page 509), which are then acetalized selectively on the aldehyde group in a manner which is known per se.

Most of the starting compounds of formula XI are known, such as, for example, 4-acetyl-benzophenone, 2-acetylfluorenone, 2-acetylthioxanthone, 4,4'-diacetylbenzophenone or 2,7-diacetylfluorenone, or they can be prepared from the known compounds by introducing the appropriate substituents. The oxidation to give the α-ketoaldehydes is preferably carried out in an inert solvent, such as, for example, toluene, xylene, ethanol, propanol, dioxane or tetrahydrofuran, traces of water in many cases giving rise to an increase in yield. The acetalization is carried out, for example, by reacting the α-ketoaldehydes with an alcohol of the formula R$^{11}$OH in the presence of catalytic amounts of a mineral acid. It is also particularly advantageous to use trialkyl orthoformates as acetalizing agents.

It is furthermore possible to convert the acetyl compounds of the formula XI into the corresponding compounds of the formula I in which X=H and R$^3$=R$^4$=OR$^{11}$ by reaction with nitrosyl chloride in the presence of an alcohol of the general formula R$^{11}$OH, for example, in accordance with the methods described in J. Org. Chem. 26 (1961), 3755 or U.S. Pat. No. 2,995,573.

The compounds of formula I can be used, according to this invention, as photoinitiators for the photopolymerization of ethylenically unsaturated compounds or for the curing of photopolymerizable systems which contain such compounds, and in particular also as UV-curing agents for printing inks. They are used in the customary manner.

As a rule, the compounds of this invention are added to the systems to be polymerized in amounts of 0.1 to 20% by weight, preferably 0.5 to 12% by weight. This addition is as a rule effected by simply dissolving and stirring them in, since most of the systems to be polymerized and most of the photoinitiators of this invention are liquid or at least readily soluble. By a system to be polymerized there is understood a mixture of monofunctional or polyfunctional ethylenically unsaturated monomers, oligomers, prepolymers or polymers which can be initiated by free radicals, or mixtures of these oligomers, prepolymers and polymers with unsaturated monomers. It is possible, as a rule, for the mixture to contain other additives, such as, for example, antioxidants, light stabilizers, dyestuffs, pigments, other known photoinitiators and reaction accelerators. Possible unsaturated compounds include all those in which the C=C double bonds are activated by, for example, halogen atoms or carbonyl, cyano, carboxyl, ester, amide ether or aryl groups or by other conjugated double or triple bonds. Examples of such compounds are vinyl chloride, vinylidene chloride, acrylonitrile, methacrylonitrile, acrylamide, methyl, ethyl, n- or tert-butyl, cyclohexyl, 2-ethylhexyl, benzyl, phenoxyethyl, hydroxyethyl, hydroxypropyl, lower alkoxyethyl or tetrahydrofurfuryl acrylate or methacrylate, vinyl acetate, propionate, acrylate or succinate, N-vinylpyrrolidone, N-vinylcarbazole, styrene, divinylbenzene, substituted styrenes and mixtures of such unsaturated compounds. Polyunsaturated compounds, such as, for example, ethylene diacrylate, 1,6-hexanediol diacrylate, propoxylated bisphenol A diacrylate and dimethacrylate, trimethylolpropane diacrylate and pentaerythritol triacrylate, can also be polymerized with the photoinitiators of this invention. Possible photopolymerizable compounds include, furthermore, unsaturated oligomers, prepolymers or polymers and mixtures thereof with unsaturated monomers. These include, for example, unsaturated polyesters, unsaturated acrylic materials, epoxy materials, urethanes, silicones, aminopolyamide resins and, in particular, acrylated resins, such as acrylated silicone oil, acrylated polyester, acrylated urethanes, acrylated polyamides. acrylated soya bean oil, acrylated epoxy resin and acrylated acrylic resin, preferably as a mixture with one or more acrylates of a mono-, di- or poly-alcohol.

The photopolymerizable compounds or systems can be stabilized by adding the customary amounts of the known heat inhibitors and anitoxidants, such as, for example, hydroquinone or hydroquinone derivatives, pyrogallol, thiophenols, nitro compounds, β-naphthylamines or β-naphthols, without the initiator action of the photoinitiators of this invention being noticeably impaired. Such additives should, above all, prevent premature polymerization during the preparation of the systems by mixing of the components.

It is also possible to add small amounts of light stabilizers, such as, for example, benzophenone derivatives, benzotriazole derivatives or phenylsalicylates.

In order to exclude the inhibiting action of atmospheric oxygen, paraffin or similar wax-like substances are frequently also added to the photopolymerizable systems. As a result of their deficient solubility in the polymer, these float to the top when the polymerization starts and form a transparent layer on the surface, which prevents entry of air. Atmospheric oxygen can also be deactivated, for example, by introducing autoxidizable groups, such as, for example, allyl groups, into the system to be cured.

The photoinitiators of this invention can also be used in combination with known initiators which form free radicals, such as, for example, peroxides, hydroperoxides, ketone peroxides or percarboxylates. They can furthermore contain pigments or dyestuffs which are customary, for example, in printing inks which are to be cured by photochemical means. In this case, the amount of photoinitiator chosen is higher, for example, 6 to 12% by weight, while 0.1 to 3% by weight is in most cases completely adequate for colorless photopolymerizable products. Fillers, such as talc, gypsum or silicic acid, or fibers, organic additives, such as thixotropic agents, flow control agents, binders, lubricants, delustering agents, plasticizers, wetting agents, silicones for improving the nature of the surface, anti-flooding agents or small amounts of solvents can be added, depending on the intended use.

Possible known photoinitiators which can optionally be used together with the initiators of this invention include, for example, benzophenones, such as, for example, Michler's ketone (4,4'-bis[dimethylamino]-benzophenone), 4,4'-bis(diethylamino)benzophenone, p-dimethylaminobenzo-phenone, p-chlorobenzophenone or benzophenone; anthraquinones, such as, for example, anthraquinone, 2-chloroanthraquinone or 2-alkylanthraquinones; xanthones, such as, for example, 2-halogenoxanthones or 2-alkylxanthones; thioxanthones, such as 2-chlorothioxanthone or 2-alkylthioxanthones; acridanones, such as, for example, 2-alkylacridanones or N-substituted acridanones; benzoins, such as, for example, p-dimethylaminobenzoin and alkyl ethers of benzoin; and benzil ketals, α-halogeno-ketones, dialkoxyacetophenones, α-hydroxyalkylphenones and α-aminoalkylphenones such as are described, for example, in German Offenlegungsschrift No. 2,722,264 and in European Offenlegungsschrift No. 3,002, and furthermore, for example, fluorenones, dibenzosuberones, phenanthrenequinones and benzoates, such as, for example, hydroxypropyl benzoate and acryloxyethyl benzoyl benzoate.

Reaction accelerators which can be added are, for example, organic amines, phosphines, alcohols and/or thiols, all of which have at least one CH group in the α-position relative to the hetero-atom. Suitable compounds include, for example, primary, secondary and tertiary aliphatic, aromatic, araliphatic or heterocyclic amines, such as are described, for example, in U.S. Pat. No. 3,759,807. Examples of such amines include butylamine, dibutylamine, tributylamine, cyclohexylamine, benzyldimethylamine, di-cyclohexylamine, triethanolamine, N-methyldiethanolamine, phenyl-diethanolamine, piperidine, piperazine, morpholine, pyridine, quinoline, ethyl p-dimethylaminobenzoate, butyl p-dimethylaminobenzoate, 4,4'-bis-dimethylaminobenzophenone (Michler's ketone) or 4,4'-bis-diethylaminobezophenone. Tertiary amines, such as, for example, trimethylamine, triethylamine, tri-isopropylamine, tributylamine, octyl-dimethylamine, dodecyl-dimethylamine, triethanolamine, N-methyl-diethanolamine, N-butyl-diethanolamine, tris(hydroxypropyl)amine, alkyl dimethylaminobenzoates and Michler's ketone, are particularly preferred.

Other possible reaction accelerators include, for example, trialkylphosphines, secondary alcohols and thiols.

Photopolymerizable systems which additionally contain a tertiary organic amine as the reaction accelerator are a particularly preferred form of the present invention.

The expression "photopolymerization of ethylenically unsaturated compounds" is to be understood in the broadest sense. This includes, for example, further polymerization or cross-linking of polymeric materials, for example, of prepolymers, homo-, co- and ter-polymerization of simple monomers and also the combination of the types of reactions mentioned.

The photopolymerization is carried out by methods which are known per se, by irradiation with visible light or UV radiation in the wavelength range from 250 to 500 nm, preferably from 300 to 400 nm. Sources of radiation which can be used include sunlight or artificial lamps. Advantageous sources include, for example, high-pressure, medium-pressure or low-pressure mercury vapor lamps and xenon and tungsten lamps; laser light sources can likewise be employed.

The compounds of this invention can be used as photoinitiators in the UV-curing of thin layers, such as, for example, coatings on paper, plastic and metal, and offer considerable advantages as initiators for photocuring printing inks and for use in photocurable systems for producing printing plates.

Photocuring of printing inks has achieved particularly great importance, since the drying time of the binder is a determining factor for the rate of production of graphic products and is on the order of fractions of seconds. In the production of printing plates, for example, mixtures of soluble linear polyamides with photopolymerizable monomers, for example, acrylamides, and a photoinitiator are used. Films or plates produced from these systems are exposed over the negative or over the positive of the original and the non-cured portions are then eluted with a solvent.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples all temperatures are set forth uncorrected in degrees Celsius; unless otherwise indicated, all parts and percentages are by weight.

The preparation and use of the compounds of this invention are described in more detail in the following examples.

Pressure data for the boiling points are given in Pascal.

EXAMPLE 1

150 ml of 10% sodium hydroxide solution is added to 70 g of 4-(2-chloro-2-methyl-propanoyl)-benzophenone and the mixture is boiled for 3 hours. It is then allowed to cool and the 4-(2-hydroxy-2-methyl-propanoyl)-benzophenone which has precipitated is filtered off while rinsing with water, dried and recrystallized from cyclohexane. M.p. 71°–72°.

The starting material can be obtained as follows:

(a) 31 g of aluminum trichloride and 25 g of 2-methyl-propanoyl chloride are added successively to a solution of 33.6 of diphenylmethane in 150 ml of methylene chloride at 0° to 5°. The reaction mixture is subsequently stirred overnight at 20° and then decomposed by adding hydrochloric acid. The organic phase is separated off and washed with water and the solvent is distilled off under reduced pressure. The residue is subjected to fractional distillation. 4-(2-Methyl-propanoyl)-diphenylmethane is obtained; b.p. 185°/40 P.

(b) The calculated amount of chlorine gas is passed into a solution of 47.6 g of 4-(2-methyl-propanoyl)-diphenylmethane in 250 ml of carbon tetrachloride at 60°.

When the reaction has ended, the solvent is distilled off. The 4-(2-chloro-2-methyl-propanoyl)-diphenylmethane, which is obtained in the form of an oil, is employed in stage (c) without further purification.

(c) 68 g of 4-(2-chloro-2-methyl-propanoyl)-diphenylmethane is dissolved in 500 ml of acetic acid, and 75 g of sodium dichromate is added, while stirring. The reaction mixture is subsequently stirred at 90° for 3 hours and is then poured into 1 l of water. The mixture is extracted several times with methylene chloride, sodium carbonate is added to the combined organic extracts and the solvent is distilled off under reduced pressure. The resulting 4-(2-chloro-2-methyl-propanoyl)-benzophenone is converted into 4-(2-hydroxy-2-methyl-propanoyl)-benzophenone without further purification.

The following compounds of formula I can be obtained analogously to Example 1:

3-(2-hydroxy-2-methyl-propanoyl)-benzophenone,
2-(2-hydroxy-2-methyl-propanoyl)-benzophenone,
2-methyl-4-(2-hydroxy-2-methyl-propanoyl)-benzophenone,
2-ethyl-4-(2-hydroxy-2-methyl-propanoyl)-benzophenone,
2-butyl-4-(2-hydroxy-2-methyl-propanoyl)-benzophenone,
2-octyl-4-(2-hydroxy-2-methyl-propanoyl)-benzophenone,
2-isopropyl-4-(2-hydroxy-2-methyl-propanoyl)-benzophenone,
2-cyclopentyl-4-(2-hydroxy-2-methyl-propanoyl)-benzophenone,
2-phenyl-4-(2-hydroxy-2-methyl-propanoyl)-benzophenone,
2-benzyl-4-(2-hydroxy-2-methyl-propanoyl)-benzophenone,
2-hydroxy-2-(2-hydroxy-2-methyl-propanoyl)-benzophenone,
2-methoxy-4-(2-hydroxy-2-methyl-propanoyl)-benzophenone,
2-ethoxy-4-(2-hydroxy-2-methyl-propanoyl)-benzophenone,
2-phenoxy-4-(2-hydroxy-2-methyl-propanoyl)-benzophenone,
2-methylthio-4-(2-hydroxy-2-methyl-propanoyl)-benzophenone,
2-ethylthio-4-(2-hydroxy-2-methyl-propanoyl)-benzophenone,
2-ethylsulfonyl-4-(2-hydroxy-2-methyl-propanoyl)-benzophenone,
2-methoxycarbonyl-4-(2-hydroxy-2-methyl-propanoyl)-benzophenone,
2-ethylamino-4-(2-hydroxy-2-methyl-propanoyl)-benzophenone,
2-dimethylamino-4-(2-hydroxy-2-methyl-propanoyl)-benzophenone,
2-cyano-4-(2-hydroxy-2-methyl-propanoyl)-benzophenone,
2-chloro-4-(2-hydroxy-2-methyl-propanoyl)-benzophenone,
3-methyl-4-(2-hydroxy-2-methyl-propanoyl)-benzophenone,
3-isopropyl-4-(2-hydroxy-2-methyl-propanoyl)-benzophenone,
3-methoxy-4-(2-hydroxy-2-methyl-propanoyl)-benzophenone,
3-dimethylamino-4-(2-hydroxy-2-methyl-propanoyl)-benzophenone,
3-chloro-4-(2-hydroxy-2-methyl-propanoyl)-benzophenone,
2,6-dimethyl-4-(2-hydroxy-2-methyl-propanoyl)-benzophenone,
2,6-dimethoxy-4-(2-hydroxy-2-methyl-propanoyl)-benzophenone,
2-methyl-6-chloro-4-(2-hydroxy-2-methyl-propanoyl)-benzophenone,
4-(2-hydroxy-2-methyl-propanoyl)-4'-methyl-benzophenone,
4-(2-hydroxy-2-methyl-propanoyl)-4'-ethyl-benzophenone,
4-(2-hydroxy-2-methyl-propanoyl)-4'-butyl-benzophenone,
4-(2-hydroxy-2-methyl-propanoyl)-4'-octyl-benzophenone,
4-(2-hydroxy-2-methyl-propanoyl)-4'-isopropyl-benzophenone,
4-(2-hydroxy-2-methyl-propanoyl)-4'-cyclopentyl-benzophenone,
4-(2-hydroxy-2-methyl-propanoyl)-4'-phenyl-benzophenone,
4-(2-hydroxy-2-methyl-propanoyl)-4'-benzyl-benzophenone,
4-(2-hydroxy-2-methyl-propanoyl)-4'-hydroxy-benzophenone,
4-(2-hydroxy-2-methyl-propanoyl)-4'-methoxy-benzophenone,
4-(2-hydroxy-2-methyl-propanoyl)-4'-ethoxy-benzophenone,
4-(2-hydroxy-2-methyl-propanoyl)-4'-phenoxy-benzophenone,
4-(2-hydroxy-2-methyl-propanoyl)-4'-methylthio-benzophenone,
4-(2-hydroxy-2-methyl-propanoyl)-4'-ethylthio-benzophenone,
4-(2-hydroxy-2-methyl-propanoyl)-4'-ethylsulfonylbenzophenone,
4-(2-hydroxy-2-methyl-propanoyl)-4'-methoxycarbonyl-benzophenone,
4-(2-hydroxy-2-methyl-propanoyl)-4'-ethylamino-benzophenone,
4-(2-hydroxy-2-methyl-propanoyl)-4'-dimethylaminobenzophenone, 4-(2-hydroxy-2-methyl-propanoyl)-4'-cyano-benzophenone,
4-(2-hydroxy-2-methyl-propanoyl)-4'-chloro-benzophenone,
4-(2-hydroxy-2-methyl-propanoyl)-3'-methyl-benzophenone,
4-(2-hydroxy-2-methyl-propanoyl)-3'-isopropyl-benzophenone,
4-(2-hydroxy-2-methyl-propanoyl)-3'-methoxy-benzophenone,
4-(2-hydroxy-2-methyl-propanoyl)-3'-dimethylaminobenzophenone,
4-(2-hydroxy-2-methyl-propanoyl)-3'-chloro-benzophenone,
4-(2-hydroxy-2-methyl-propanoyl)-2'-methyl-benzophenone,
4-(2-hydroxy-2-methyl-propanoyl)-2'-methoxy-benzophenone,
4-(2-hydroxy-2-methyl-propanoyl)-2'-chloro-benzophenone,
4-(2-hydroxy-2-methyl-propanoyl)-2',4'-dimethyl-benzophenone,
4-(2-hydroxy-2-methyl-propanoyl)-2',4'-dimethoxybenzophenone,
4-(2-hydroxy-2-methyl-propanoyl)-2'-methyl-4'-chlorobenzophenone,
4-(2-hydroxy-2-methyl-propanoyl)-2',4',6'-trimethylbenzophenone,
4-(2-hydroxy-propanoyl)-benzophenone,
4-(2-hydroxy-acetyl)-benzophenone,
4-(2-hydroxy-2-methyl-butanoyl)-benzophenone,
4-(2-hydroxy-2-methyl-pentanoyl)-benzophenone,
4-(2-hydroxy-2-methyl-hexanoyl)-benzophenone,
4-(2-hydroxy-2-methyl-octanoyl)-benzophenone,
4-(2-hydroxy-2-methyl-pent-3-enoyl)-benzophenone,
4-(2-hydroxy-2-cyclohexyl-propanoyl)-benzophenone,
4-(2-hydroxy-2-methyl-3-phenyl-propanoyl)-benzophenone,
4-(2-hydroxy-2-(2-hydroxyethyl)-propanoyl)-benzophenone, 4-(2-hydroxy-2-(2-methoxyethyl)-propanoyl)-benzophenone,
4-(2-hydroxy-2-(2-acetoxyethyl)-propanoyl)-benzophenone,
4-(2-hydroxy-2-(2-dimethylaminoethyl)-propanoyl)-benzophenone,
4-(2-hydroxy-2-(2-ethoxycarbonylethyl)-propanoyl)-benzophenone,
4-(2-hydroxy-2-(2-cyanoethyl)-propanoyl)-benzophenone,
4-(2-hydroxy-2-ethyl-butanoyl)-benzophenone,
4-(2-hydroxy-2-butyl-hexanoyl)-benzophenone,
4-(2-hydroxy-2-hexyl-octanoyl)-benzophenone,
4-(1-hydroxy-cyclohexyl-carbonyl)-benzophenone,
4-(1-hydroxy-cyclopentyl-carbonyl)-benzophenone,
4-(2-hydroxy-2-methyl-propanoyl)-benzil,
2-methyl-4-(2-hydroxy-2-methyl-propanoyl)-benzil,
2-methoxy-4-(2-hydroxy-2-methyl-propanoyl)-benzil,
2-dimethylamino-4-(2-hydroxy-2-methyl-propanoyl)-benzil,
2-chloro-4-(2-hydroxy-2-methyl-propanoyl)-benzil,
4-(2-hydroxy-2-methyl-propanoyl)-4'-methyl-benzil,
4-(2-hydroxy-2-methyl-propanoyl)-4'-isopropyl-benzil,
4-(2-hydroxy-2-methyl-propanoyl)-4'-chloro-benzil,
4-(2-hydroxy-2-ethyl-butanoyl)-benzil,
4-(1-hydroxy-cyclohexyl-carbonyl)-benzil and
4-(1-hydroxy-cyclopentyl-carbonyl)-benzil.

EXAMPLE 2

32.2 g of 4,4'-bis-(2-methyl-propanoyl)-benzophenone is dissolved in 250 ml of carbon tetrachloride, and the calculated amount of chlorine gas is passed into this solution at 60°. When the reaction has ended, the solvent is distilled off. The 4,4'-bis-(2-chloro-2-methylpropanoyl)-benzophenone which is obtained in the form of an oil, is boiled in excess sodium hydroxide solution without further purification, and, when the hydrolysis has ended, the mixture is extracted with ether. The ether extract is evaporated. The 4,4'-bis-(2-hydroxy-2-methyl-propanoyl)-benzophenone which remains is recrystallized from ethanol; m.p. 82°–83°.

The starting material can be obtained, analogously to Example 1, as follows:

Diphenylmethane is converted into 4,4'-bis-(2-methyl-propanoyl)-diphenylmethane (b.p. 190°/4 P) in a Friedel-Crafts reaction, and the product is oxidized with sodium dichromate to give 4,4'-bis-(2-methyl-propanoyl)-benzophenone.

The following compounds of formula I can be obtained analogously to Example 2:
3,4'-bis-(2-hydroxy-2-methyl-propanoyl)-benzophenone,
2-methyl-4,4'-bis-(2-hydroxy-2-methyl-propanoyl)-benzophenone,
2-isopropyl-4,4'-bis-(2-hydroxy-2-methyl-propanoyl)-benzophenone,
2-methoxy-4,4'-bis-(2-hydroxy-2methyl-propanoyl)-benzophenone,
2-chloro-4,4'-bis-(2-hydroxy-2methyl-propanoyl)-benzophenone,
2'-methyl-4,4'-bis-(2-hydroxy-2-methyl-propanoyl)-benzophenone,
2'-chloro-4,4'-bis-(2-hydroxy-2-methyl-propanoyl)-benzophenone,
4,4'-bis-(2-hydroxy-2-ethyl-butanoyl)-benzophenone,
4,4'-bis-(1-hydroxy-cyclohexyl-carbonyl)-benzophenone,
4,4'-bis-(1-hydroxy-cyclopentyl-carbonyl)-benzophenone,
4,4'-bis-(2-hydroxy-2-methyl-propanoyl)-benzil,
4,4'-bis-(2-hydroxy-2-ethyl-butanoyl)-benzil,
4,4'-bis-(1-hydroxy-cyclohexyl-carbonyl)-benzil,
4,4'-bis-(1-hydroxy-cyclopentyl-carbonyl)-benzil and
3,4'-bis-(2-hydroxy-2-methyl-propanoyl)-benzil.

EXAMPLE 3

Analogously to Example 1, 2-(2-hydroxy-2-methyl-propanoyl)-thioxanthone is obtained from 2-(2-chloro-2-methyl-propanoyl)-thioxanthone by hydrolysis; m.p. 134°–136°.

EXAMPLE 4

Analogously to Example 1, 2-(2-hydroxy-2-methyl-propanoyl)-anthraquinone is obtained from 2-(2-chloro-2-methyl-propanoyl)-anthraquinone by hydrolysis; m.p. 172°–174°.

The following compounds can be obtained analogously from the corresponding starting compounds:
2-(2-hydroxy-2-methyl-propanoyl)-fluorenone,
2-(2-hydroxy-2-methyl-propanoyl)-anthrone,
2-(2-hydroxy-2-methyl-propanoyl)-dibenzosuberone,
2-(2-hydroxy-2-methyl-propanoyl)-xanthone,
2-(2-hydroxy-2-methyl-propanoyl)-acridanone,
2-(2-hydroxy-2-methyl-propanoyl)-N-methyl-acridanone, 2-(2-hydroxy-2-methyl-propanoyl)-N-ethyl-acridanone,
2-(2-hydroxy-2-methyl-propanoyl)-N-cyclohexyl-acridanone,
2-(2-hydroxy-2-methyl-propanoyl)-9,10-dihydro-dibenzo[a,c]cyclohexene-9,10-dione,
2-(2-hydroxy-2-methyl-propanoyl)-10,11-dihydro-5H-dibenzo[a,d]cycloheptene-10,11-dione,
2-(2-hydroxy-2-methyl-propanoyl)-5,6,11,12-tetrahydrodibenzo[a,e]cyclooctene-11,12-dione,
2-(2-hydroxy-2-methyl-propanoyl)-10,11-dihydro-dibenzo[b,f]thiepine-10,11-dione,
2-(2-hydroxy-2-methyl-propanoyl)-10,11-dihydro-dibenzo[b,f]oxepine-10,11-dione,
2-(2-hydroxy-2-methyl-propanoyl)-10,11-dihydro-5H-dibenzo[a,d]cycloheptene-5,10,11-trione,
2-(2-hydroxy-2-methyl-propanoyl)-10,11-dihydro-5H-dibenzo[b,f]azepine-10,11-dione,
2-(2-hydroxy-2-methyl-propanoyl)-10,11-dihydro-5-methyl-5H-dibenzo[b,f]azepine-10,11-dione,
2-(2-hydroxy-2-ethyl-butanoyl)-fluorenone,
2-(2-hydroxy-2-ethyl-butanoyl)-anthrone,
2-(2-hydroxy-2-ethyl-butanoyl)-dibenzosuberone,
2-(2-hydroxy-2-ethyl-butanoyl)-thioxanthone,
2-(2-hydroxy-2-ethyl-butanoyl)-xanthone,
2-(2-hydroxy-2-ethyl-butanoyl)-anthraquinone,
2-(2-hydroxy-2-ethyl-butanoyl)-acridanone,
2-(2-hydroxy-2-ethyl-butanoyl)-N-methyl-acridanone,
2-(2-hydroxy-2-ethyl-butanoyl)-9,10-dihydro-dibenzo[a,c]cyclohexene-9,10-dione,
2-(2-hydroxy-2-ethyl-butanoyl)-10,11-dihydro-5H-dibenzo[a,d]cycloheptene-10,11-dione,
2-(2-hydroxy-2-ethyl-butanoyl)-5,6,11,12-tetrahydro-dibenzo[a,e]cyclooctene-11,12-dione,
2-(2-hydroxy-2-ethyl-butanoyl)-10,11-dihydro-dibenzo[b,f]thiepine-10,11-dione,
2-(2-hydroxy-2-ethyl-butanoyl)-10,11-dihydro-dibenzo[b,f]oxepine-10,11-dione,
2-(2-hydroxy-2-ethyl-butanoyl)-10,11-dihydro-5H-dibenzo[a,d]cycloheptene-5,10,11-trione,
2-(2-hydroxy-2-ethyl-butanoyl)-10,11-dihydro-5H-dibenzo[b,f]azepine-10,11-dione,
2-(2-hydroxy-2-ethyl-butanoyl)-10,11-dihydro-5-methyl-5H-dibenzo[b,f]azepine-10,11-dione,
2-(1-hydroxy-cyclohexyl-carbonyl)-fluorenone,
2-(1-hydroxy-cyclohexyl-carbonyl)-anthrone,
2-(1-hydroxy-cyclohexyl-carbonyl)-dibenzosuberone,
2-(1-hydroxy-cyclohexyl-carbonyl)-thioxanthone,
2-(1-hydroxy-cyclohexyl-carbonyl)-xanthone,
2-(1-hydroxy-cyclohexyl-carbonyl)-anthraquinone,
2-(1-hydroxy-cyclohexyl-carbonyl)-acridanone,
2-(1-hydroxy-cyclohexyl-carbonyl)-N-methyl-acridanone,
2-(1-hydroxy-cyclohexyl-carbonyl)-9,10-dihydro-dibenzo[a,c]cyclohexene-9,10-dione,
2-(1-hydroxy-cyclohexyl-carbonyl)-10,11-dihydro-5H-dibenzo[a,d]cycloheptene-10,11-dione,
2-(1-hydroxy-cyclohexyl-carbonyl)-5,6,11,12-tetrahydro-dibenzo[a,e]cyclooctene-11,12-dione,
2-(1-hydroxy-cyclohexyl-carbonyl)-10,11-dihydro-dibenzo[b,f]thiepine-10,11-dione,
2(1-hydroxy-cyclohexyl-carbonyl)-10,11-dihydro-dibenzo[b,f]oxepine-10,11-dione,
2-(1-hydroxy-cyclohexyl-carbonyl)-10,11-dihydro-5H-dibenzo[a,d]cycloheptene-5,10,11-trione,
2-(1-hydroxy-cyclohexyl-carbonyl)-10,11-dihydro-5H-dibenzo[b,f]azepine-10,11-dione and
2-(1-hydroxy-cyclohexyl-carbonyl)-10,11-dihydro-5-methyl-5H-dibenzo[b,f]azepine-10,11-dione.

EXAMPLE 5

Analogously to Example 2, 2,7-bis-(2-hydroxy-2-methyl-propanoyl)-fluorenone is obtained from 2,7-bis-(2-methyl-propanoyl)-fluorenone by chlorination and subsequent hydrolysis; m.p. 203°–204°.

The following compounds can be obtained analogously:
2,7-bis-(2-hydroxy-2-methyl-propanoyl)-anthrone,
2,7-bis-(2-hydroxy-2-methyl-propanoyl)-dibenzosuberone,
2,7-bis-(2-hydroxy-2-methyl-propanoyl)-thioxanthone,
2,7-bis-(2-hydroxy-2-methyl-propanoyl)-xanthone,
2,7-bis-(2-hydroxy-2-methyl-propanoyl)-anthraquinone,
2,7-bis-(2-hydroxy-2-methyl-propanoyl)-acridanone,
2,7-bis-(2-hydroxy-2-methyl-propanoyl)-N-methyl-acridanone,
2,7-bis-(2-hydroxy-2-methyl-propanoyl)-9,10-dihydro-dibenzo[a,c]cyclohexene-9,10-dione,
2,8-bis-(2-hydroxy-2-methyl-propanoyl)-10,11-dihydro-5H-dibenzo[a,d]cycloheptene-10,11-dione,
2,9-bis-(2-hydroxy-2-methyl-propanoyl)-5,6,11,12-tetrahydro-dibenzo[a,e]cyclooctene-11,12-dione,
2,8-bis-(2-hydroxy-2methyl-propanoyl)-10,11-dihydro-dibenzo[b,f]thiepine-10,11-dione,
2,8-bis-(2-hydroxy-2-methyl-propanoyl)-10,11-dihydro-dibenzo[b,f]oxepine-10,11-dione,
2,8-bis-(2-hydroxy-2-methyl-propanoyl)-10,11-dihydro-5H-dibenzo[a,d]cycloheptene-5,10,11-trione,
2,8-bis-(2-hydroxy-2-methyl-propanoyl)-10,11-dihydro-5H-dibenzo[b,f]azepine-10,11-dione,
2,8-bis-(2-hydroxy-2-methyl-propanoyl)-10,11-dihydro-5-methyl-5H-dibenzo[b,f]azepine-10,11-dione,
2,7-bis-(2-hydroxy-2-ethyl-butanoyl)-fluorenone,
2,7-bis-(2-hydroxy-2-ethyl-butanoyl)-anthrone,
2,7-bis-(2-hydroxy-2-ethyl-butanoyl)-dibenzosuberone,
2,7-bis-(2-hydroxy-2-ethyl-butanoyl)-thioxanthone,
2,7-bis-(2-hydroxy-2-ethyl-butanoyl)-xanthone,
2,7-bis-(2-hydroxy-2-ethyl-butanoyl)-anthraquinone,
2,7-bis-(2-hydroxy-2-ethyl-butanoyl)-acridanone,
2,7-bis-(2-hydroxy-2-ethyl-butanoyl)-N-methyl-acridanone,
2,7-bis-(2-hydroxy-2-ethyl-butanoyl)-9,10,-dihydro-dibenzo[a,c]cyclohexene-9,10-dione,
2,8-bis-(2-hydroxy-2-ethyl-butanoyl)-10,11-dihydro-5H-dibenzo[a,d]cycloheptene-10,11-dione,
2,9-bis-(2-hydroxy-2-ethyl-butanoyl)-5,6,11,12-tetrahydro-dibenzo[a,e]cyclooctene-11,12-dione,
2,9-bis-(2-hydroxy-2-ethyl-butanoyl)-10,11-dihydrodi benzo[b,f]thiepine-10,11-dione,
2,8-bis-(2-hydroxy-2-ethyl-butanoyl)-10,11-dihydro-dibenzo[b,f]oxepine-10,11-dione,
2,8-bis-(2-hydroxy-2-ethyl-butanoyl)-10,11-dihydro-5H-dibenzo[a,d]cycloheptene-5,10,11-trione,
2,8-bis-(2-hydroxy-2-ethyl-butanoyl)-10,11-dihydro-5H-dibenzo[b,f]azepine-10,11-dione,
2,8-bis-(2-hydroxy-2-ethyl-butanoyl)-10,11-dihydro-5-methyl-5H-dibenzo[b,f]azepine-10,11-dione,
2,7-bis-(1-hydroxy-cyclohexyl-carbonyl)-fluorenone,
2,7-bis-(1-hydroxy-cyclohexyl-carbonyl)-anthrone,
2,7-bis-(1-hydroxy-cyclohexyl-carbonyl)-dibenzosuberone,
2,7-bis-(1-hydroxy-cyclohexyl-carbonyl)-thioxanthone,
2,7-bis-(1-hydroxy-cyclohexyl-carbonyl)-xanthone,
2,7-bis-(1-hydroxy-cyclohexyl-carbonyl)-anthraquinone,
2,7-bis-(1-hydroxy-cyclohexyl-carbonyl)-acridanone, 2,7-bis-(1-hydroxy-cyclohexyl-carbonyl)-N-methyl-acridanone,
2,7-bis-(1-hydroxy-cyclohexyl-carbonyl)-9,10-dihydro-dibenzo[a,c]cyclohexene-9,10-dione,
2,8-bis-(1-hydroxy-cyclohexyl-carbonyl)-10,11-dihydro-5H-dibenzo[a,d]cycloheptene-10,11-dione,
2,9-bis-(1-hydroxy-cyclohexyl-carbonyl)-5,6,11,12-tetrahydro-dibenzo[a,e]cyclooctene-11,12-dione,
2,8-bis-(1-hydroxy-cyclohexyl-carbonyl)-10,11-dihydro-dibenzo[b,f]thiepine-10,11-dione,
2,8-bis-(1-hydroxy-cyclohexyl-carbonyl)-10,11-dihydro-dibenzo[b,f]oxepine-10,11-dione,
2,8-bis-(1-hydroxy-cyclohexyl-carbonyl)-10,11-dihydro-5H-dibenzo[a,d]cycloheptene-5,10,11-trione,
2,8-bis-(1-hydroxy-cyclohexyl-carbonyl)-10,11-dihydro-5H-dibenzo[b,f]azepine-10,11-dione and
2,8-bis-(1-hydroxy-cyclohexyl-carbonyl)-10,11-dihydro-5-methyl-5H-dibenzo[b,f]azepine-10,11-dione.

EXAMPLE 6

78 g of 4,4'-bis-(2-chloro-2-methyl-propanoyl)-benzophenone is boiled with 250 ml of morpholine for 15 hours. The excess morpholine is then distilled off under reduced pressure and the residue is crystallized from ethanol. 4,4'-bis-(2-Morpholino-2-methyl-propanoyl)-benzophenone is obtained; m.p. 145°-147°.

The following compounds can be obtained analogously, by a reaction with the corresponding amines:
4-(2-dimethylamino-2-methyl-propanoyl)-benzophenone,
4-(2-diethylamino-2-methyl-propanoyl)-benzophenone,
4-(2-dibutylamino-2-methyl-propanoyl)-benzophenone,
4-(2-di-(2-hydroxyethyl)-amino-2-methyl-propanoyl)-benzophenone,
4-(2di-(1-cyanoethyl)-amino-2-methyl-propanoyl)-benzophenone,
4-(2-diallylamino-2-methyl-propanoyl)-benzophenone,
4-(2-piperidino-2-methyl-propanoyl)-benzophenone,
4-(2-pyrrolidino-2-methyl-propanoyl)-benzophenone,
4-(2-piperazino-2-methyl-propanoyl)-benzophenone,
4-(2-(N-methylpiperazino)-2-methyl-propanoyl)-benzophenone,
4,4'-bis-(2-dimethylamino-2-methyl-propanoyl)-benzophenone,
4,4'-bis-(2-diethylamino-2-methyl-propanoyl)-benzophenone,
4,4'-bis-(2-piperidino-2-methyl-propanoyl)-benzophenone,
4,4'-bis-(2-morpholino-2-methyl-propanoyl)-benzophenone,
4,4'-bis-(2-piperazino-2-methyl-propanoyl)-benzophenone,
4,4'-bis-(2-(N-methylpiperazino)-2-methyl-propanoyl)-benzophenone,
4-(2-dimethylamino-2-methyl-propanoyl)-benzil,
4-(2-diethylamino-2-methyl-propanoyl)-benzil,
4-(2-piperidino-2-methyl-propanoyl)-benzil,
4-(2-morpholino-2-methyl-propanoyl)-benzil,
4-(2-piperazino-2-methyl-propanoyl)-benzil,
4-(2-(N-methylpiperazino)-2-methyl-propanoyl)-benzil,
4,4'-bis-(2-dimethylamino-2-methyl-propanoyl)-benzil,
4,4'-bis-(2-piperidino-2-methyl-propanoyl)-benzil,
4,4'-bis-(2-morpholino-2-methyl-propanoyl)-benzil,
2-(2-dimethylamino-2-methyl-propanoyl)-fluorenone,
2-(2-dimethylamino-2-methyl-propanoyl)-anthrone,
2-(2-dimethylamino-2-methyl-propanoyl)-dibenzosuberone,
2-(2-dimethylamino-2-methyl-propanoyl)-thioxanthone,
2-(2-dimethylamino-2-methyl-propanoyl)-xanthone,
2-(2-dimethylamino-2-methyl-propanoyl)-anthraquinone,
2-(2-dimethylamino-2-methyl-propanoyl)-acridanone,
2-(2-dimethylamino-2-methyl-propanoyl)-N-methyl-acridanone,
2-(2-dimethylamino-2-methyl-propanoyl)-9,10-dihydro-dibenzo[a,c]cyclohexene-9,10-dione,
2-(2-dimethylamino-2-methyl-propanoyl)-10,11-dihydro-5H-dibenzo[a,d]cycloheptene-10,11-dione,
2-(2-dimethylamino-2-methyl-propanoyl)-5,6,11,12-tetra-hydro-dibenzo[a,e]cycloocetene-11,12-dione,
2-(2-dimethylamino-2-methyl-propanoyl)-10,11-dihydro-dibenzo[b,f]thiepine-10,11-dione,
2-(2-dimethylamino-2-methyl-propanoyl)-10,11-dihydro-dibenzo[b,f]oxepine-10,11-dione,
2-(2-dimethylamino-2-methyl-propanoyl)-10,11-dihydro-5H-dibenzo[a,d]cycloheptene-5,10,11-trione,
2-(2-dimethylamino-2-methyl-propanoyl)-10,11-dihydro-5H-dibenzo[b,f]azepine-10,11-dione,
2(2-dimethylamino-2-methyl-propanoyl)-10,11-dihydro-5-methyl-5H-dibenzo[b,f]azepine-10,11-dione,
2,7-bis-(2-dimethylamino-2-methyl-propanoyl)-fluorenone,
2,7-bis-(2-dimethylamino-2-methyl-propanoyl)-anthrone,
2,7-bis-(2-dimethylamino-2-methyl-propanoyl)-dibenzosuberone,
2,7-bis-(2-dimethylamino-2-methyl-propanoyl)-thioxanthone,
2,7-bis-(2-dimethylamino-2-methyl-propanoyl)-xanthone,
2,7-bis-(2-dimethylamino-2-methyl-propanoyl)-anthraquinone,
2,7-bis-(2-dimethylamino-2-methyl-propanoyl)-acridanone,
2,7-bis-(2-dimethylamino-2-methyl-propanoyl)-N-methyl-acridanone,
2,7-bis-(2-dimethylamino-2-methyl-propanoyl)-9,10-dihydro-dibenzo[a,c]cyclohexene-9,10-dione,
2,8-bis-(2-dimethylamino-2-methyl-propanoyl)-10,11-dihydro-5H-dibenzo[a,d]cycloheptene-10,11-dione,
2,9-bis-(2-dimethylamino-2-methyl-propanoyl)-5,6,11,12-tetrahydro-dibenzo[a,e]cyclooctene-11,12-dione,
2,8-bis-(2-dimethylamino-2-methyl-propanoyl)-10,11-dihydro-dibenzo[b,f]thiepine-10,11-dione,
2,8-bis-(2-dimethylamino-2-methyl-propanoyl)-10,11-dihydro-dibenzo[b,f]oxepine-10,11-dione,
2,8-bis-(2-dimethylamino-2-methyl-propanoyl)-10,11-dihydro-5H-dibenzo[a,d]cycloheptene-5,10,11-trione,
2,8-bis-(2-dimethylamino-2-methyl-propanoyl)-10,11-dihydro-5H-dibenzo[b,f]azepine-10,11-dione,
2,8-bis-(2-dimethylamino-2-methyl-propanoyl)-10,11-dihydro-5-methyl-5H-dibenzo[b,f]azepine-10,11-dione,
2-(2-piperidino-2-methyl-propanoyl)-fluorenone,
2-(2-piperidino-2-methyl-propanoyl)-anthrone,
2-(2-piperidino-2-methyl-propanoyl)-dibenzosuberone,
2-(2-piperidino-2-methyl-propanoyl)-thioxanthone,
2-(2-piperidino-2-methyl-propanoyl)-xanthone,
2-(2-piperidino-2-methyl-propanoyl)-anthraquinone,
2-(2-piperidino-2-methyl-propanoyl)-acridanone,
2-(2-piperidine-2-methyl-propanoyl)-N-methyl-acridanone, 2-(2-piperidino-2-methyl-propanoyl)-9,10-dihydro-dibenzo[a,c]cyclohexene-9,10-dione,
2-(2-piperidino-2-methyl-propanoyl)-10,11-dihydro-5H-dibenzo[a,d]cycloheptene-10,11-dione,
2-(2-piperidino-2-methyl-propanoyl)-5,6,11,12-tetrahydro-dibenzo[a,e]cyclooctene-11,12-dione,
2-(2-piperidino-2-methyl-propanoyl)-10,11-dihydro-dibenzo[b,f]thiepine-10,11-dione,
2-(2-piperidino-2-methyl-propanoyl)-10,11-dihydro-dibenzo[b,f]oxepine-10,11-dione,
2-(2-piperidino-2-methyl-propanoyl)-10,11-dihydro-5H-dibenzo[a,d]cycloheptene-5,10,11-trione,
2-(2-piperidino-2-methyl-propanoyl)-10,11-dihydro-5H-dibenzo[b,f]azepine-10,11-dione,
2-(2-piperidino-2-methyl-propanoyl)-10,11-dihydro-5H-dibenzo[b,f]azepine-10,11-dione,
2,7-bis-(2-piperidino-2-methyl-propanoyl)-fluorenone,
2,7-bis-(2-piperidino-2-methyl-propanoyl)-anthrone,
2,7-bis-(2-piperidino-2-methyl-propanoyl)-dibenzosuberone,
2,7-bis-(2-piperidino-2-methyl-propanoyl)-thioxanthone,
2,7-bis-(2-piperidino-2-methyl-propanoyl)-xanthone,
2,7-bis-(2-piperidino-2-methyl-propanoyl)-anthraquinone,
2,7-bis-(2-piperidino-2-methyl-propanoyl)-acridanone,
2,7-bis-(2-piperidino-2-methyl-propanoyl)-N-methyl-acridanone,
2,7-bis-(2-piperidino-2-methyl-propanoyl)-9,10-dihydro-dibenzo[a,c]cyclohexene-9,10-dione,
2,8-bis-(2-piperidino-2-methyl-propanoyl)-10,11-dihydro-5H-dibenzo[a,d]cycloheptene-10,11-dione,
2,9-bis-(2-piperidino-2-methyl-propanoyl)-5,6,11,12-tetrahydro-dibenzo[a,e]cyclooctene-11,12-dione,
2,8-bis-(2-piperidino-2-methyl-propanoyl)-10,11-dihydro-dibenzo[b,f]thiepine-10,11-dione,
2,8-bis-(2-piperidino-2-methyl-propanoyl)-10,11-dihydro-dibenzo[b,f]oxepine-10,11-dione,
2,8-bis-(2-piperidino-2-methyl-propanoyl)-10,11-dihydro-5H-dibenzo[a,d]cycloheptene-5,10,11-trione,
2,8-bis-(2-piperidino-2-methyl-propanoyl)-10,11-dihydro-5H-dibenzo[b,f]azepine-10,11-dione,
2,8-bis-(2-piperidino-2-methyl-propanoyl)-10,11-dihydro-5-methyl-5H-dibenzo[b,f]azepine-10,11-dione,
2-(2-morpholino-2-methyl-propanoyl)-fluorenone,
2-(2-morpholino-2-methyl-propanoyl)-anthrone,
2-(2-morpholino-2-methyl-propanoyl)-dibenzosuberone,
2-(2-morpholino-2-methyl-propanoyl)-thioxanthone,
2-(2-morpholino-2-methyl-propanoyl)-xanthone,
2-(2-morpholino-2-methyl-propanoyl)-anthraquinone,
2-(2-morpholino-2-methyl-propanoyl)-acridanone,
2-(2-morpholino-2-methyl-propanoyl)-N-methyl-acridanone,
2-(2-morpholino-2-methyl-propanoyl)-9,10-dihydro-dibenzo[a,c]cyclohexene-9,10-dione,
2-(2-morpholino-2-methyl-propanoyl)-10,11-dihydro-5H-dibenzo[a,d]cycloheptene-10,11-dione,
2-(2-morpholino-2-methyl-propanoyl)-5,6,11,12-tetrahydro-dibenzo[a,e]cyclooctene-11,12-dione,
2-(2-morpholino-2-methyl-propanoyl)-10,11-dihydro-dibenzo[b,f]thiepine-10,11-dione,
2-(2-morpholino-2-methyl-propanoyl)-10,11-dihydro-dibenzo[b,f]oxepine-10,11-dione,
2-(2-morpholino-2-methyl-propanoyl)-10,11-dihydro-5H-dibenzo[a,d]cycloheptene-5,10,11-trione,
2-(2-morpholino-2-methyl-propanoyl)-10,11-dihydro-5H-dibenzo[b,f]azepine-10,11-dione,
2-(2-morpholino-2-methyl-propanoyl)-10,11-dihydro-5-methyl-5H-dibenzo[b,f]azepine-10,11-dione,
2,7-bis-(2-morpholino-2-methyl-propanoyl)-fluorenone,
2,7-bis-(2-morpholino-2-methyl-propanoyl)-anthrone,
2,7-bis-(2-morpholino-2-methyl-propanoyl)-dibenzosuberone,
2,7-bis-(2-morpholino-2-methyl-propanoyl)-thioxanthone,
2,7-bis-(2-morpholino-2-methyl-propanoyl)-xanthone,
2,7-bis-(2-morpholino-2-methyl-propanoyl)-anthraquinone,
2,7-bis-(2-morpholino-2-methyl-propanoyl)-acridanone,
2,7-bis-(2-morpholino-2-methyl-propanoyl)-N-methyl-acridanone,
2,7-bis-(2-morpholino-2-methyl-propanoyl)-9,10-dihydro-dibenzo[a,c]cyclohexene-9,10-dione,
2,8-bis-(2-morpholino-2-methyl-propanoyl)-10,11-dihydro-5H-dibenzo[a,d]cycloheptene-10,11-dione,
2,9-bis-(2-morpholino-2-methyl-propanoyl)-5,6,11,12-tetrahydro-dibenzo[a,e]cyclooctene-11,12-dione,
2,8-bis-(2-morpholino-2-methyl-propanoyl)-10,11-dihydro-dibenzo[b,f]thiepine-10,11-dione,
2,8-bis-(2-morpholino-2-methyl-propanoyl)-10,11-dihydro-dibenzo[b,f]oxepine-10,11-dione,
2,8-bis-(2-morpholino-2-methyl-propanoyl)-10,11-dihydro-5H-dibenzo[a,d]cycloheptene-5,10,11-trione,
2,8-bis-(2-morpholino-2-methyl-propanoyl)-10,11-dihydro-5H-dibenzo[b,f]azepine-10,11-dione and
2,8-bis-(2-morpholino-2-methyl-propanoyl)-10,11-dihydro-5-methyl-5H-dibenzo[b,f]azepine-10,11-dione.

EXAMPLE 7

28.7 g of 4-(2-chloro-2-methyl-propanoyl)-benzophenone and 5.4 g of sodium methoxide are boiled in 120 ml of methanol for 4 hours. After cooling, the mixture is filtered, the filtrate is evaporated and water is added to the residue. The mixture is extracted with ether and, after drying and evaporating the combined extracts, 4-(2-methoxy-2-methyl-propanoyl)-benzophenone is obtained as a viscous oil.

The following compounds can be obtained analogously:
4-(2-ethoxy-2-methyl-propanoyl)-benzophenone,
4-(2-propoxy-2-methyl-propanoyl)-benzophenone,
4-(2-butoxy-2-methyl-propanoyl)-benzophenone,
4-(2-hexyloxy-2-methyl-propanoyl)-benzophenone,
4-(2-(2-methoxyethoxy)-2-methyl-propanoyl)-benzophenone,
4-(2-acetoxymethoxy-2-methyl-propanoyl)-benzophenone,
4-(2-ethoxycarbonylethoxy-2-methyl-propanoyl)-benzophenone,
4-(2-allyloxy-2-methyl-propanoyl)-benzophenone,
4-(2-cyclohexyloxy-2-methyl-propanoyl)-benzophenone,
4-(2-benzyloxy-2-methyl-propanoyl)-benzophenone,
4-(2-phenoxy-2-methyl-propanoyl)-benzophenone,
4-(2-methoxy-2-methyl-propanoyl)-benzil,
2-(2-methoxy-2-methyl-propanoyl)-fluorenone,
2-(2-methoxy-2-methyl-propanoyl)-anthrone,
2-(2-methoxy-2-methyl-propanoyl)-dibenzosuberone,
2-(2-methoxy-2-methyl-propanoyl)-thioxanthone,
2-(2-methoxy-2-methyl-propanoyl)-xanthone,
2-(2-methoxy-2-methyl-propanoyl)-anthraquinone,
2-(2-methoxy-2-methyl-propanoyl)-acridanone,
2-(2-methoxy-2-methyl-propanoyl)-N-methyl-acridanone, 2-(2-methoxy-2-methyl-propanoyl)-9,10-dihydro-dibenzo[a,c]cyclohexene-9,10-dione,
2-(2-methoxy-2-methyl-propanoyl)-10,11-dihydro-5H-dibenzo[a,d]cycloheptene-10,11-dione,
2-(2-methoxy-2-methyl-propanoyl)-5,6,11,12-tetrahydro-dibenzo[a,e]cyclooctene-11,12-dione,
2-(2-methoxy-2-methyl-propanoyl)-10,11-dihydro-dibenzo[b,f]thiepine-10,11-dione,
2-(2-methoxy-2-methyl-propanoyl)-10,11-dihydro-dibenzo[b,f]oxepine-10,11-dione,
2-(2-methoxy-2-methyl-propanoyl)-10,11-dihydro-5H-dibenzo[a,d]cycloheptene-5,10,11-trione,
2-(2-methoxy-2-methyl-propanoyl)-10,11-dihydro-5H-dibenzo[b,f]azepine-10,11-dione and
2-(2-methoxy-2-methyl-propanoyl)-10,11-dihydro-5-methyl-5H-dibenzo[b,f]azepine-10,11-dione.

EXAMPLE 8

45 g of bis-(trimethylsilyl)-acetamide, 500 ml of toluene and 500 ml of pyridine are added to 39 g of 2,7-bis-(2-hydroxy-2-methyl-propanoyl)-fluorenone, and the mixture is boiled for 24 hours. It is then concentrated and the residue is crystallized from toluene. 2,7-bis-(2-Trimethylsilyloxy-2-methyl-propanoyl)-fluorenone is obtained; m.p. 128°–129°.

The following compounds can be obtained analogously:
4-(2-trimethylsilyloxy-2-methyl-propanoyl)-benzophenone,
4-(2-trimethylsilyloxy-2-methyl-propanoyl)-benzil,
2-(2-trimethylsilyloxy-2-methyl-propanoyl)-fluorenone,
2-(2-trimethylsilyloxy-2-methyl-propanoyl)-anthrone,
2-(2-trimethylsilyloxy-2-methyl-propanoyl)-dibenzosuberone,
2-(2-trimethylsilyloxy-2-methyl-propanoyl)-thioxanthone,
2-(2-trimethylsilyloxy-2-methyl-propanoyl)-xanthone,
2-(2-trimethylsilyloxy-2-methyl-propanoyl)-anthraquinone,
2-(2-trimethylsilyloxy-2-methyl-propanoyl)-acridanone,
2-(2-trimethylsilyloxy-2-methyl-propanoyl)-N-methyl-acridanone,
2-(2-trimethylsilyloxy-2-methyl-propanoyl)-9,10-dihydro-dibenzo[a,c]cyclohexene-9,10-dione,
2-(2-trimethylsilyloxy-2-methyl-propanoyl)-10,11-dihydro-5H-dibenzo[a,d]cycloheptene-10,11-dione,
2-(2-trimethylsilyloxy-2-methyl-propanoyl)-5,6,11,12-tetrahydro-dibenzo[a,e]cyclooctene-11,12-dione,
2-(2-trimethylsilyloxy-2-methyl-propanoyl)-10,11-dihydro-dibenzo[b,f]thiepine-10,11-dione,
2-(2-trimethylsilyloxy-2-methyl-propanoyl)-10,11-dihydro-dibenzo[b,f]oxepine-10,11-dione,
2-(2-trimethylsilyloxy-2-methyl-propanoyl)-10,11-dihydro-5H-dibenzo[a,d]cycloheptene-5,10,11-trione,
2-(2-trimethylsilyloxy-2-methyl-propanoyl)-10,11-dihydro-5H-dibenzo[b,f]azepine-10,11-dione,
2-(2-trimethylsilyloxy-2-methyl-propanoyl)-10,11-dihydro-5-methyl-5H-dibenzo[b,f]azepine-10,11-dione,
4,4'-bis-(2-trimethylsilyloxy-2-methyl-propanoyl)-benzophenone,
4,4'-bis-(2-trimethylsilyloxy-2-methyl-propanoyl)-benzil,
2,7-bis-(2-trimethylsilyloxy-2-methyl-propanoyl)-anthrone,
2,7-bis-(2-trimethylsilyloxy-2-methyl-propanoyl)-dibenzosuberone,
2,7-bis-(2-trimethylsilyloxy-2-methyl-propanoyl)-thioxanthone,
2,7-bis-(2-trimethylsilyloxy-2-methyl-propanoyl)-xanthone,
2,7-bis-(2-trimethylsilyloxy-2-methyl-propanoyl)-anthraquinone,
2,7-bis-(2-trimethylsilyloxy-2-methyl-propanoyl)-acridanone,
2,7-bis-(2-trimethylsilyloxy-2-methyl-propanoyl)-N-methyl-acridanone,
2,7-bis-(2-trimethylsilyloxy-2-methyl-propanoyl)-9,10-dihydro-dibenzo[a,c]cyclohexene-9,10-dione,
2,8-bis-(2-trimethylsilyloxy-2-methyl-propanoyl)-10,11-dihydro-5H-dibenzo[a,d]cycloheptene-10,11-dione,
2,9-bis-(2-trimethylsilyloxy-2-methyl-propanoyl)-5,6,11,12-tetrahydro-dibenzo[a,e]cyclooctene-11,12-dione,
2,8-bis-(2-trimethylsilyloxy-2-methyl-propanoyl)-10,11-dihydro-dibenzo[b,f]thiepine-10,11-dione,
2,8-bis-(2-trimethylsilyloxy-2-methyl-propanoyl)-10,11-dihydro-dibenzo[b,f]oxepine-10,11-dione,
2,8-bis-(5-trimethylsilyloxy-2-methyl-propanoyl)-10,11-dihydro-5H-dibenzo[a,d]cycloheptene-5,10,11-trione,
2,8-bis-(5-trimethylsilyloxy-2-methyl-propanoyl)-10,11-dihydro-5H-dibenzo[b,f]azepine-10,11-dione,
2,8-bis-(5-trimethylsilyloxy-2-methyl-propanoyl)-10,11-dihydro-5-methyl-5H-dibenzo[b,f]azepine-10,11-dione,
4-(2-diethyl-methylsilyloxy-2-methyl-propanoyl)-benzophenone,
4-(2-dibutyl-methylsilyloxy-2-methyl-propanoyl)-benzophenone and
4-(2-phenyldimethylsilyloxy-2-methyl-propanoyl)-benzophenone.

EXAMPLE 9

78 g of 4-acetyl-benzophenone is boiled together with 500 ml of ethanol and 200 ml of triethyl orthoformate for 5 hours. The solvent is then distilled off under reduced pressure and the residue is subjected to fractional distillation. 4-(Diethoxyacetyl)-benzophenone is obtained; b.p. 200°/67 P.

The starting material can be obtained as follows: A mixture of 77 g of 4-acetyl-diphenylmethane, 200 ml of dioxane, 7 ml of water and 37 g of selenium dioxide is heated to 95° for 5 hours. After filtering the mixture and concentrating the filtrate, 78 g of 4-acetyl-benzophenone remains as a wax-like product which can be further processed without purification.

The following compounds can be obtained analogously:
4-(dimethoxyacetyl)-benzophenone,
4-(dipropoxyacetyl)-benzophenone,
4-(dibutoxyacetyl)-benzophenone,
4-(dimethoxyethoxyacetyl)-benzophenone,
4-(dichloroethoxyacetyl)-benzophenone,
4-(diethoxyacetyl)-benzil,
2-(diethoxyacetyl)-fluorenone,
2-(diethoxyacetyl)-anthrone,
2-(diethoxyacetyl)-dibenzosuberone,
2-(diethoxyacetyl)-thioxanthone,
2-(diethoxyacetyl)-xanthone,
2-(diethoxyacetyl)-anthraquinone,
2-(diethoxyacetyl)-acridanone,
2-(diethoxyacetyl)-N-methyl-acridanone,
2-(diethoxyacetyl)-9,10-dihydro-dibenzo[a,c]cyclohexene-9,10-dione, 2-(diethoxyacetyl)-10,11-dihydro-5H-dibenzo[a,d]cycloheptene-10,11-dione,
2-(diethoxyacetyl)-5,6,11,12-tetrahydro-dibenzo[a,e]cyclooctene-11,12-dione,
2-(diethoxyacetyl)-10,11-dihydro-dibenzo[b,f]thiepine-10,11-dione,
2-(diethoxyacetyl)-10,11-dihydro-dibenzo[b,f]oxepine-10,11-dione,
2-(diethoxyacetyl)-10,11-dihydro-5H-dibenzo[a,d]cycloheptene-5,10,11-trione,
2-(diethoxyacetyl)-10,11-dihydro-5H-dibenzo[b,f]azepine-10,11-dione and
2-(diethoxyacetyl)-10,11-dihydro-5-methyl-5H-dibenzo[b,f]azepine-10,11-dione.

EXAMPLE 10

Analogously to Example 9, 4,4'-bis-(diethoxyacetyl)-benzophenone is obtained as a viscous oil from 4,4'-bis-acetyl-benzophenone by reaction with ethanol and triethyl orthoformate.

The following compounds can be obtained analogously:
4,4'-bis-(diethoxyacetyl)-benzil,
2,7-bis-(diethoxyacetyl)-fluorenone,
2,7-bis-(diethoxyacetyl)-anthrone,
2,7-bis-(diethoxyacetyl)-dibenzosuberone,
2,7-bis-(diethoxyacetyl)-thioxanthone,
2,7-bis-(diethoxyacetyl)-xanthone,
2,7-bis-(diethoxyacetyl)-anthraquinone,
2,7-bis-(diethoxyacetyl)-acridanone,
2,7-bis-(diethoxyacetyl)-N-methyl-acridanone,
2,7-bis-(diethoxyacetyl)-9,10-dihydro-dibenzo[a,c]-cyclohexene-9,10-dione,
2,8-bis-(diethoxyacetyl)-10,11-dihydro-5H-dibenzo[a,d]-cycloheptene-10,11-dione,
2,9-bis-(diethoxyacetyl)-5,6,11,12-tetrahydro-dibenzo[a,e]cyclooctene-11,12-dione,
2,8-bis-(diethoxyacetyl)-10,11-dihydro-dibenzo[b,f]-thiepine-10,11-dione,
2,8-bis-(diethoxyacetyl)-10,11-dihydro-dibenzo[b,f]oxepine-10,11-dione,
2,8-bis-(diethoxyacety)-10,11-dihydro-5H-dibenzo[a,d]-cycloheptene-5,10,11-trione,
2,8-bis-(diethoxyacetyl)-10,11-dihydro-5H-dibenzo[b,f]-azepine-10,11-dione and
2,8-bis-(diethoxyacetyl)-10,11-dihydro-5-methyl-5H-dibenzo[b,f]azepine-10,11-dione.

EXAMPLE 11

40 g of nitrosyl chloride is introduced into a solution of 32.2 g of 4,4'-bis-acetyl-benzophenone in 250 ml of methanol at 20°. The mixture is then heated to the reflux temperature for 3 hours. The solvent is subsequently distilled off, 125 ml of 2 N sodium hydroxide solution is added to the residue and the mixture is heated again to the reflux temperature for 2 hours. After cooling, the reaction mixture is extracted with ether and the combined organic phases are concentrated. 4,4'-bis-(Dimethoxyacetyl)-benzophenone is obtained as the residue, in the form of a yellow-brown oil.

The following Examples A to D relate to the use of the compounds according to this invention as photoinitiators in the photopolymerization of ethylenically unsaturated compounds and UV-curing agents for printing inks.

EXAMPLE A

A resin mixture consisting of 80 parts of an epoxy-acrylate resin (Laromer ® 2555 from BASF, Ludwigshafen), 20 parts of trimethylolpropane trisacrylate and 1.5 parts of photoinitiator is drawn, in a thickness of 50 μm, onto glass plates by means of a film-drawing unit, under yellow light, in order to eliminate uncontrollable effects of daylight. Subsequent curing of these films is carried out with a Minicure unit (from Primaro ITP (England)), in which the lacquer samples are passed, on a conveyor belt with a variable speed, under a high-pressure mecury lamp (intensity of radiation: 80 W/cm), and are thereby irradiated. The radiation dose is varied by changing the belt speed and the lacquer sample is cured to a varying degree.

The hardness of the films at various belt speeds are given in the following table. They are measured with a pendulum device in accordance with the method of König (DIN No. 53,157).

A polymer film obtained with a photoinitiator of this invention is compared with several polymer films obtained using known photoinitiators. Since the hardness of a lacquer system cured with UV-radiation is greater, under otherwise identical conditions, the more reactive the photoinitiator is, it can be used indirectly as a measure of the reactivity of a photoinitiator.

| Photoinitiator used | Belt speed (m/minute) | Pendulum hardness (s) |
|---|---|---|
| 4,4'-bis-(2-hydroxy-2-methyl-propanoyl)-benzophenone | 20 | 147 |
| | 40 | 115 |
| | 60 | 100 |
| 1-(4-dodecylphenyl)-2-hydroxy-2-methyl-propan-1-one | 20 | 109 |
| | 40 | 68 |
| | 60 | 51 |
| benzoin isopropyl ether | 20 | 98 |
| | 40 | 53 |
| | 60 | 48 |
| diethoxyacetophenone | 20 | 92 |
| | 40 | 50 |
| | 60 | 35 |
| trichloroacetophenone | 20 | 73 |
| | 40 | 42 |
| | 60 | 25 |
| benzophenone | 20 | 17 |
| | 40 | no curing |
| | 60 | no curing |

EXAMPLE B 1.5 parts of 4-(2-hydroxy-2-methyl-propanoyl)-benzophenone are added to a resin mixture of 63.5 parts of SVP ® 1928 (a resin from Degussa, Frankfurt) and 36.5 parts of butanediol diacrylate and the mixture is applied, in a thickness of 15 μm, to aluminium foil. After irradiation with UV light, a firmly adhering, nontacky, colorless film is obtained.

EXAMPLE C 63.5 parts of an epoxy-acrylate resin (Laromer ® 8555 from BASF, Ludwigshafen) are triturated with 36.5 parts of butanediol diacrylate and 20 parts of Heliogenblau on a triple roll mill. 5 parts of 4-(2-hydroxy-2-methyl-propanoyl)-benzophenone are stirred into the suspension at 50° over the course of 10 minutes. The printing ink thus obtained is printed, in a layer thickness of 1 μm, onto a substrate and cured in a Minicure unit (from Primaro ITP (England) at a belt speed of 50 m/minute and with a radiation output of 160 W/cm.

Analogously to Example C, the photoinitiators mentioned in Examples 1 to 11 can be used as UV-curing agents for printing inks.

EXAMPLE D 63.5 parts of a urethane acrylate resin (Uvimer ® 530 from Bayer, Leverkusen) are ground with 36.5 parts of butanediol diacrylate and 100 parts of titanium dioxide (anatase) in a porcelain ball mill. 8.5 parts of a solution of 2.5 parts of 4-(2-hydroxy-2-methyl-propanoyl)-benzophenone, 3 parts of benzoin isopropyl ether and 3 parts of N-methyldiethanolamine are then stirred in. When applied in a layer thickness of 10 μm to glass plates, the lacquer can be cured at a belt speed of 50 m/minute and with a radiation output of 160 W/cm to give a film which is free from tackiness.

Analogously to Example D, the compounds mentioned in Examples 1 to 11 can be incorporated into a lacquer as photoinitiators.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

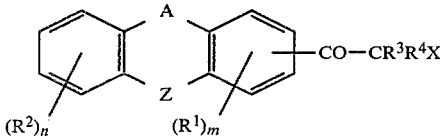

wherein
A is —CO— or —CO—CO—;
X is —OR$^5$; with R$^3$, is —O—CH(R$^{10}$)—,
Z is —NR$^{12}$—;
m is 0 or an integer of 1 to 3;
n is 0 or an integer of 1 to 3;
R$^1$ is alkyl of 1–12 C atoms, cycloalkyl of 5–6 C atoms, aryl of 6–14 C atoms, aralkyl of 7–9 C atoms, —OH, —OAlk, —OAr, —SAlk, —SCH$_2$CH$_2$OH, —SAr, —SO$_2$Alk, —SO$_2$phenyl, —SO$_2$NH$_2$, —SO$_2$NHalk, —SO$_2$N(Alk)$_2$, —COOAlk, —NH$_2$, —NHAlk, —N(Alk)$_2$, —NHCOphenyl, —CN or halogen;
R$^2$ can be any of the groups defined for R$^1$ or another —CO—CR$^3$R$^4$X group;
R$^3$ is H, alkyl of 1–8 C atoms, or alkyl of 1–8 C atoms substituted by —OH, —OAlk, acyloxy of 2–8 C atoms, —NR$^8$R$^9$, —COOAlk or —CN, or is alkenyl of 3–5 C atoms
R$^4$ can be any of the groups defined for R$^3$ or —CH$_2$CH$_2$R$^{13}$;

R$^5$ is H, alkyl of 1–12 C atoms, or alkyl of 1–8 C atoms substituted by —Cl, —Br, —OH, —OAlk, —SAlk, acyloxy of 2–8 C atoms, —COOAlk, —CONHAlk, —CON(Alk)$_2$ or —CN, or is alkenyl of 3–5 C atoms, or cyclohexyl;
R$^8$ is alkyl of 1–12 C atoms, or alkyl or 2–4 C atoms substituted by —OH, —OAlk or —CN, or is alkenyl of 3–5 C atoms or, cyclohexyl;
R$^9$ is alkyl of 1–12 C atoms, or alkyl of 2–4 C atoms substituted by —OH, —OAlk or —CN, or is alkenyl of 3–5 C atoms or, cyclohexyl, or, together with R$^8$, is alkylene of 4–5 C atoms or C$_{4-5}$-alkylene interrupted by —O— or —NR$^{14}$—, or, together with R$^4$, is alkylene of 1–9 C atoms, or oxaor azaalkylene of 2–3 C atoms;
R$^{12}$ is H, alkyl of 1–4 C atoms or cycloalkyl of 5–6 C atoms;
R$^{13}$ is —CONH$_2$, —CONHAlk, —CON(Alk)$_2$,
R$^{14}$ is alkyl of 1–4 C atoms,
Alk is alkyl of 1–4 C atoms; and
Ar is C$_{6-14}$ aryl or aryl substituted by alkyl groups and having a total of 6–14 C atoms;
wherein aryl stands for hydrocarbon aryl groups and acyl groups are derived from hydrocarbon carboxylic acids.

2. A compound of claim 1 wherein A is —CO— or —CO—CO—; X is —OR$^5$ —NR$^{12}$—; m is 0 or 1; n is 0 or 1; R$^1$ is alkyl of 1–8 C atoms, cycloalkyl of 5–6 C of atoms, aryl of 6–10 C atoms, aralkyl of 7–9 C atoms, —OAlk, —OAr, —SAlk, —COOAlk, —NH$_2$, —NHAlk, —N(Alk)$_2$, —CN or halogen; R$^2$ is one of the groups defined for R$^1$ or is another —CO—CR$^3$R$^4$X group; R$^3$ is H, alkyl of 1–8 C atoms, alkyl of 1–4 C atoms substituted by —OH, —OAlk, —NR$^8$R$^9$ or —CN, or alkenyl of 3–5 C atoms; R$^4$ is one of the groups defined for R$^3$; R$^5$ is H, alkyl of 1–8 C atoms, alkyl of 1–8 C atoms substituted by —OH, —OAlk, —SAlk, —COOAlk or —CN, or alkenyl of 3–5 C atoms, or cyclohexyl; R$^8$ is alkyl of 1–8 C atoms, alkyl of 2–4 C atoms substituted by —OH, —OAlk or —CN, or alkenyl of 3–5 C atoms; R$^9$ is alkyl of 1–8 C atoms, alkyl of 2–4 C atoms substituted by —OH, —OAlk or —CN, or alkenyl of 3–5 C atoms or, together with R$^8$, alkylene of 4–5 C atoms which can be interrupted by —O— or —NR$^{14}$—; R$^{12}$ is H or alkyl of 1–4 C atoms; R$^{14}$ is alkyl of 1–4 C atoms; Alk is alkyl of 1–4 C atoms; and Ar is C$_{6-10}$-aryl or aryl substituted by alkyl groups and having a total of 6–10 C atoms.

3. A compound of claim 1 wherein A is —CO—; X is —OR$^5$; Z is —NR$^{12}$; m is 0 or 1; n is 0 or 1; R$^1$ is alkyl of 1–4 C atoms, phenyl, —OAlk, —SAlk, —N(Alk)$_2$ or halogen; R$^2$ is one of these groups defined for R$^1$ or is another —CO—CR$^3$R$^4$X group; R$^3$ is H or alkyl of 1–6 of C atoms R$^4$ is one of these groups defined for R$^3$; R$^5$ is H, alkyl of 1–4 C atoms, alkenyl of 3–5 atoms, or cyclohexyl; R$^8$ is alkyl of 1–4 C atoms, alkyl of 2–4 C atoms substituted by —OH, —OAlk or —CN; R$^9$ is alkyl of 1–4 C atoms, alkyl of 2–4 C atoms substituted by —OH, —OAlk or —CN, or, together with R$^8$, alkylene of 4–5 C atoms which can be interrupted by —O— or —NR$^{14}$—; R$^{12}$ is H or alkyl of 1–4 C atoms; R$^{14}$ is alkyl of 1–4 C atoms and Alk is alkyl of 1–4 C atoms.

* * * * *

UNITED STATES PATENT AND TRADEMARK OFFICE
CERTIFICATE OF CORRECTION

PATENT NO.  : 4,374,984

DATED       : February 22, 1983

INVENTOR(S) : JURGEN EICHLER ET AL

It is certified that error appears in the above-identified patent and that said Letters Patent is hereby corrected as shown below:

Column 31, line 45: reads "X is $OR^5$; with $R^3$, is $-O-CH(R^{10})-,$"

should read -- X is $OR^5$; ---

Signed and Sealed this

Seventeenth Day of May 1983

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,374,984

DATED : February 22, 1983

INVENTOR(S) : Jurgen Eichler et al

It is certified that error appears in the above-identified patent and that said Letters Patent is hereby corrected as shown below:

Column 32, line 26: reads " —CO—CO—; X is —$OR^5$—$NR^{12}$—;

m is 0 or 1; n is 0 "

should read -- —CO—CO—; X is —$OR^5$—;

Z is —$NR^{12}$—; m is 0 or 1; n is 0 -- .

Signed and Sealed this

Seventeenth Day of April 1984

[SEAL]

Attest:

GERALD J. MOSSINGHOFF

Attesting Officer     Commissioner of Patents and Trademarks